(12) United States Patent
Galando et al.

(10) Patent No.: US 6,374,937 B1
(45) Date of Patent: Apr. 23, 2002

(54) MOTORIZED SUPPORT FOR IMAGING MEANS AND METHODS OF MANUFACTURE AND USE THEREOF

(75) Inventors: John Galando, 733 - 96th Ave. SE., Bellevue, WA (US) 98004; Joseph Giamona, Carnation, WA (US)

(73) Assignee: John Galando, Bellevue, WA (US)

( * ) Notice: Subject to any disclaimer, the term of this patent is extended or adjusted under 35 U.S.C. 154(b) by 0 days.

(21) Appl. No.: 09/427,500

(22) Filed: Oct. 26, 1999

Related U.S. Application Data

(63) Continuation-in-part of application No. 09/087,393, filed on May 29, 1998.

(51) Int. Cl.7 .............................. B62D 61/06; H05G 1/02
(52) U.S. Cl. ....................... 180/211; 180/253; 180/19.1; 180/411; 180/6.5; 180/65.1; 280/62; 280/64; 280/47.34; 378/198
(58) Field of Search ................................ 378/193, 196, 378/197, 198; 180/210, 211, 212, 213, 214, 215, 216, 253, 411, 412, 6.48, 6.5, 19.1, 19.3, 19.2, 65.1; 280/79.11, 62, 64, 47.34, 47.11

(56) References Cited

U.S. PATENT DOCUMENTS

| | | | |
|---|---|---|---|
| 2,051,508 A | * 8/1936 | Wildeboer | 378/197 |
| 2,232,014 A | 2/1941 | Simon | 250/92 |
| 2,818,510 A | 12/1957 | Verse | 250/91 |
| 3,037,784 A | 6/1962 | Williams | 280/11.26 |
| 3,081,106 A | 3/1963 | Budd | 280/11.26 |
| 3,143,749 A | 8/1964 | Buchholz et al. | 9/1 |
| 3,463,506 A | 8/1969 | Drake | 280/91 |

(List continued on next page.)

FOREIGN PATENT DOCUMENTS

JP   3-251230 A   11/1991   ............ A61B/6/00

OTHER PUBLICATIONS

Phillips brochure titled "BV212, Broaden your vision" (date of publication unknown).

Primary Examiner—Lanna Mai
Assistant Examiner—Ruth Lan
(74) Attorney, Agent, or Firm—James Richard Vance

(57) ABSTRACT

Motorized chassis, base, cart and/or carriage apparatus and methods for supporting mobile medical imaging systems. Such apparatus having precision propulsion mechanism to mechanically guide, advance and retract medical imaging equipment about a body of a patient. The invention further including methods of manufacture and use thereof.

22 Claims, 21 Drawing Sheets

U.S. PATENT DOCUMENTS

| | | | |
|---|---|---|---|
| 3,696,881 A | | 10/1972 | Gordon ................. 180/79.2 R |
| 3,879,053 A | | 4/1975 | Chvala ........................ 280/111 |
| 4,028,773 A | * | 6/1977 | Morgan ................... 280/79.11 |
| 4,248,444 A | * | 2/1981 | Johnson ................... 280/47.11 |
| 4,257,619 A | | 3/1981 | Fisher .......................... 280/91 |
| 4,365,345 A | * | 12/1982 | Craig et al. ................. 378/196 |
| 4,481,656 A | * | 11/1984 | Janssen et al. .............. 378/196 |
| 4,697,661 A | * | 10/1987 | Pajerski et al. ............... 180/6.5 |
| 4,716,581 A | * | 12/1987 | Barud ........................ 378/198 |
| 4,866,751 A | * | 9/1989 | Louiday ..................... 378/196 |
| 4,868,845 A | * | 9/1989 | Koropp ...................... 378/204 |
| 4,872,192 A | * | 10/1989 | Hahn et al. ................. 378/181 |
| 4,887,287 A | | 12/1989 | Cobben ...................... 378/198 |
| 4,912,754 A | * | 3/1990 | Van Steenburg ............ 378/209 |
| 4,955,046 A | | 9/1990 | Siczek et al. ............... 378/197 |
| 4,960,271 A | * | 10/1990 | Sebring ...................... 269/323 |
| 4,964,152 A | | 10/1990 | Kaul et al. .................. 378/198 |
| 5,008,921 A | * | 4/1991 | Kaul et al. .................. 378/198 |
| 5,048,069 A | * | 9/1991 | Siczek ........................ 378/197 |
| 5,048,071 A | | 9/1991 | Van Steenburg ............ 378/209 |
| 5,147,002 A | | 9/1992 | Hughes ....................... 180/6.5 |
| 5,156,166 A | | 10/1992 | Sebring ...................... 128/845 |
| 5,174,593 A | * | 12/1992 | Chapman ................. 280/47.11 |
| RE34,433 E | * | 11/1993 | Heiligental et al. ...... 280/79.11 |
| RE34,511 E | * | 1/1994 | O'Neill et al. .............. 378/197 |
| 5,283,823 A | | 2/1994 | Morris ....................... 378/198 |
| 5,325,935 A | | 7/1994 | Hirooka et al. ............. 180/211 |
| 5,339,350 A | * | 8/1994 | Thelosen .................... 378/198 |
| 5,350,033 A | | 9/1994 | Kraft .......................... 180/167 |
| 5,386,453 A | | 1/1995 | Harrawood et al. ........ 378/196 |
| 5,425,068 A | * | 6/1995 | Schaefer et al. ............ 378/197 |
| 5,425,069 A | | 6/1995 | Pellegrino et al. .......... 378/198 |
| 5,426,683 A | | 6/1995 | O'Farrell, Jr. et al. ...... 378/197 |
| 5,475,730 A | * | 12/1995 | Galando ..................... 378/157 |
| 5,499,284 A | | 3/1996 | Pellegrini et al. ........... 378/198 |
| 5,503,416 A | | 4/1996 | Aoki et al. ............... 280/79.11 |
| 5,544,217 A | | 8/1996 | Kadowaki et al. .......... 378/198 |
| 5,583,909 A | | 12/1996 | Hanover ..................... 378/197 |
| 5,586,162 A | | 12/1996 | Grichnik .................... 378/198 |
| 5,702,117 A | | 12/1997 | Geelhoed .................... 280/160 |
| 5,835,557 A | | 11/1998 | Malmström ................. 378/197 |
| 5,901,200 A | | 5/1999 | Krause ....................... 378/198 |
| 5,901,805 A | * | 5/1999 | Murakami et al. .......... 180/214 |
| 6,095,685 A | * | 8/2000 | Tamura ...................... 378/196 |
| 6,109,379 A | * | 8/2000 | Madwed ..................... 180/253 |

\* cited by examiner

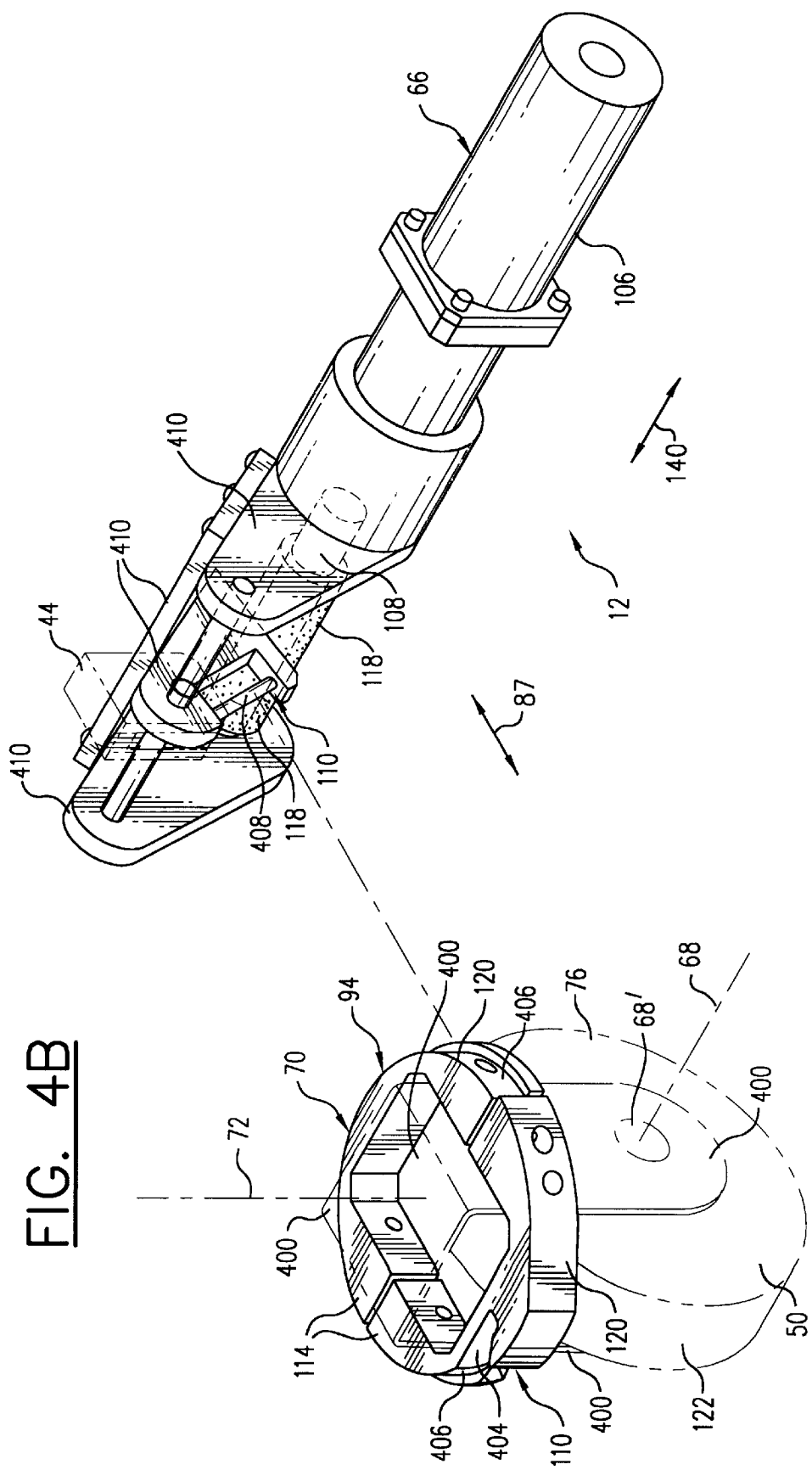

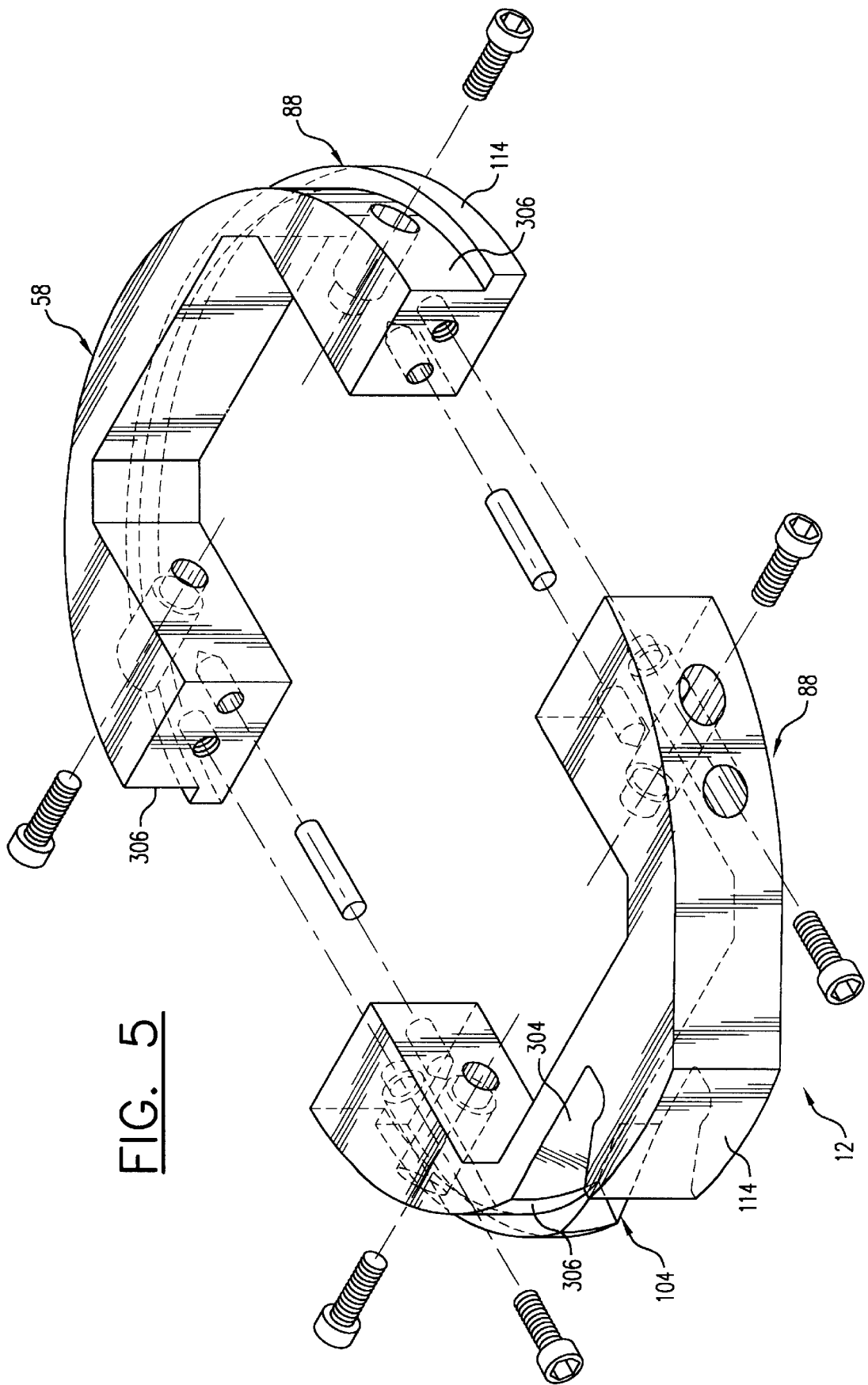

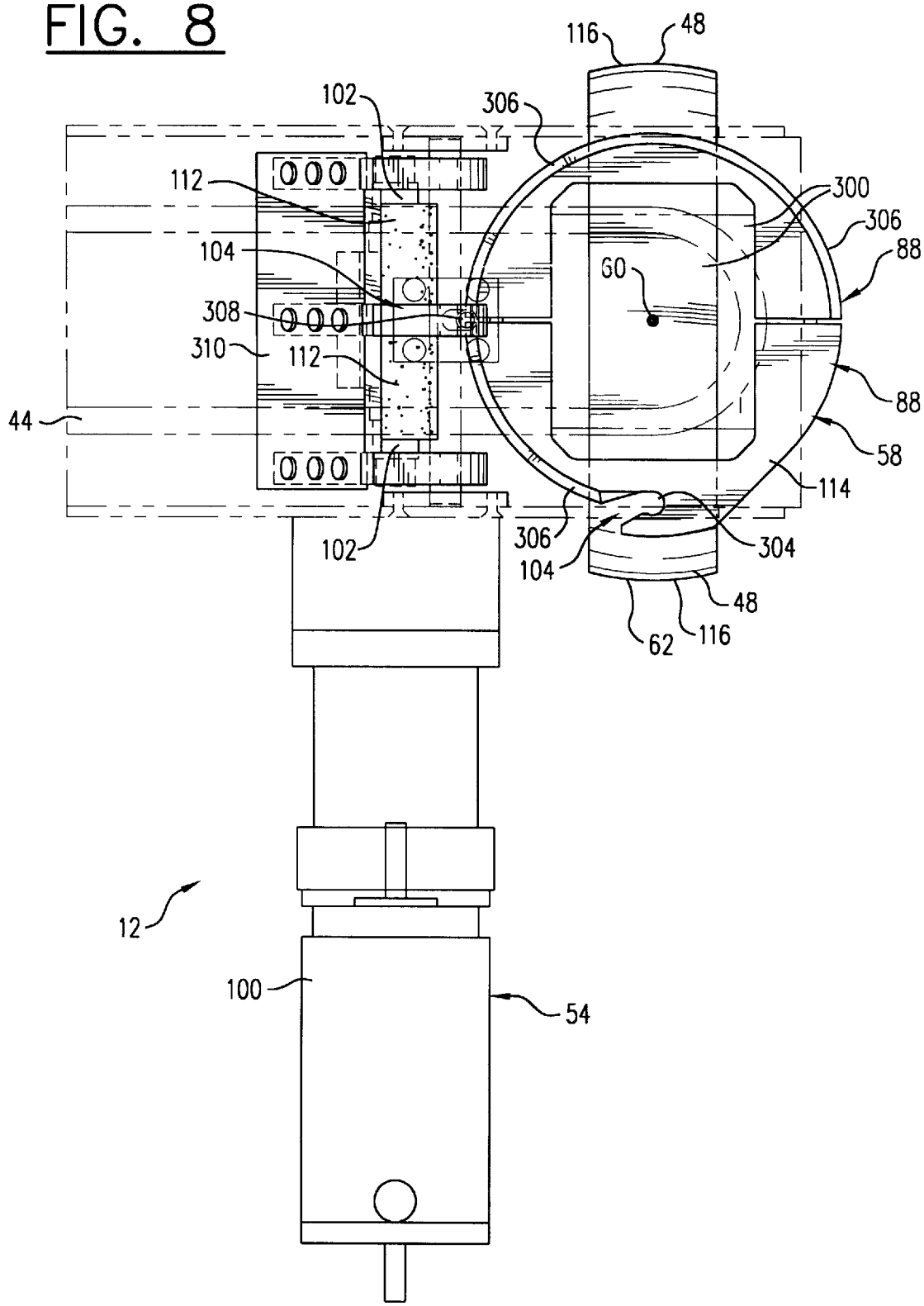

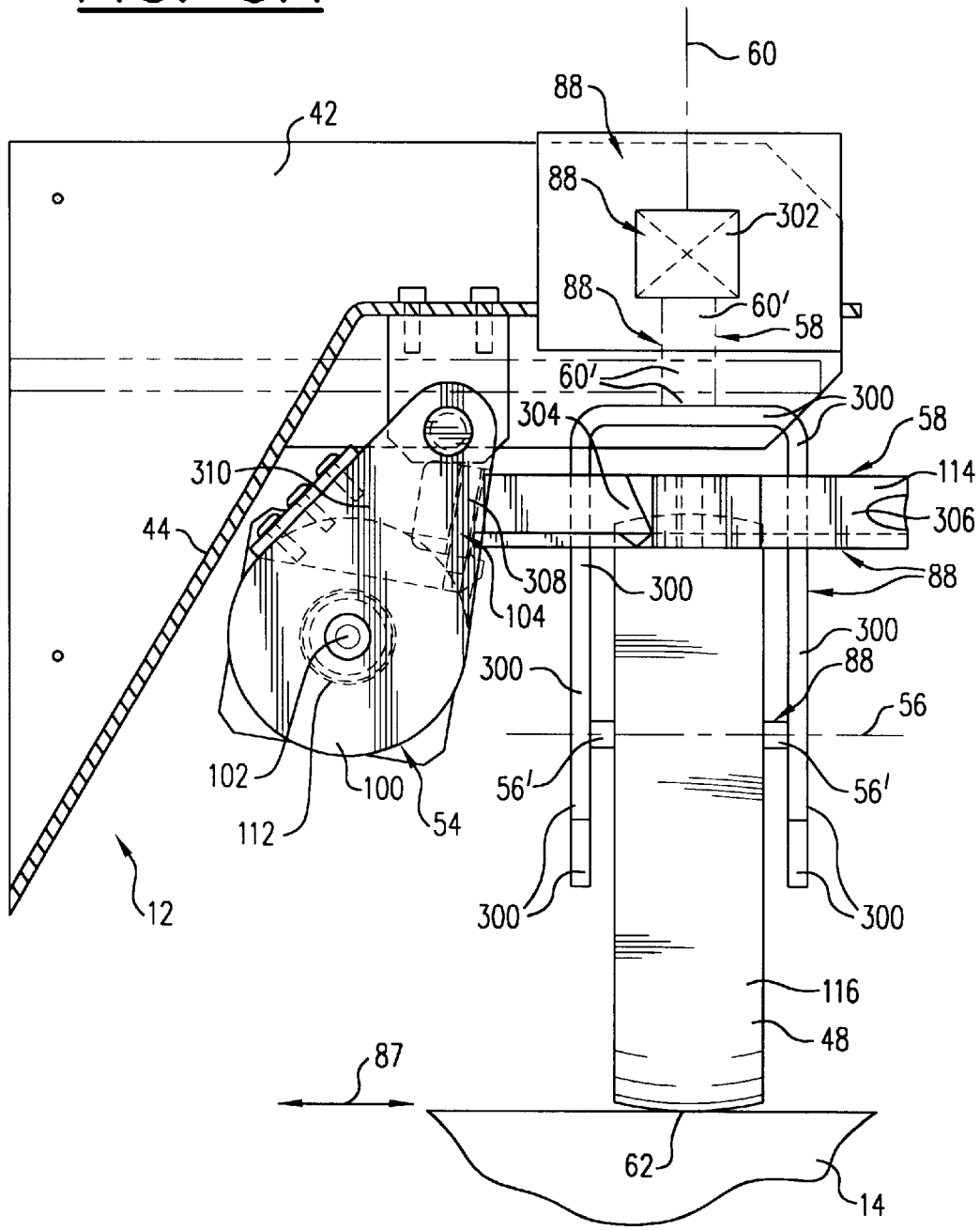

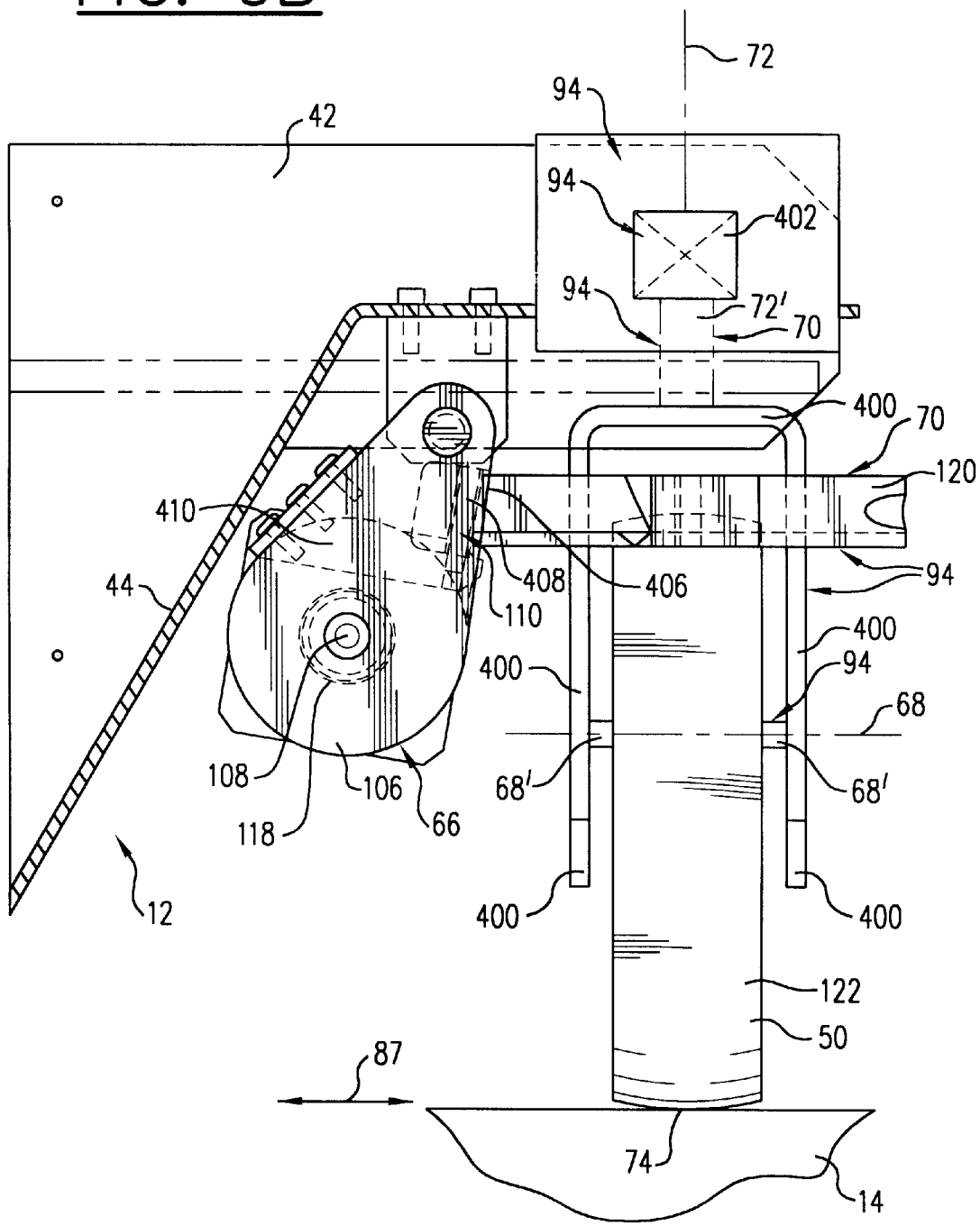

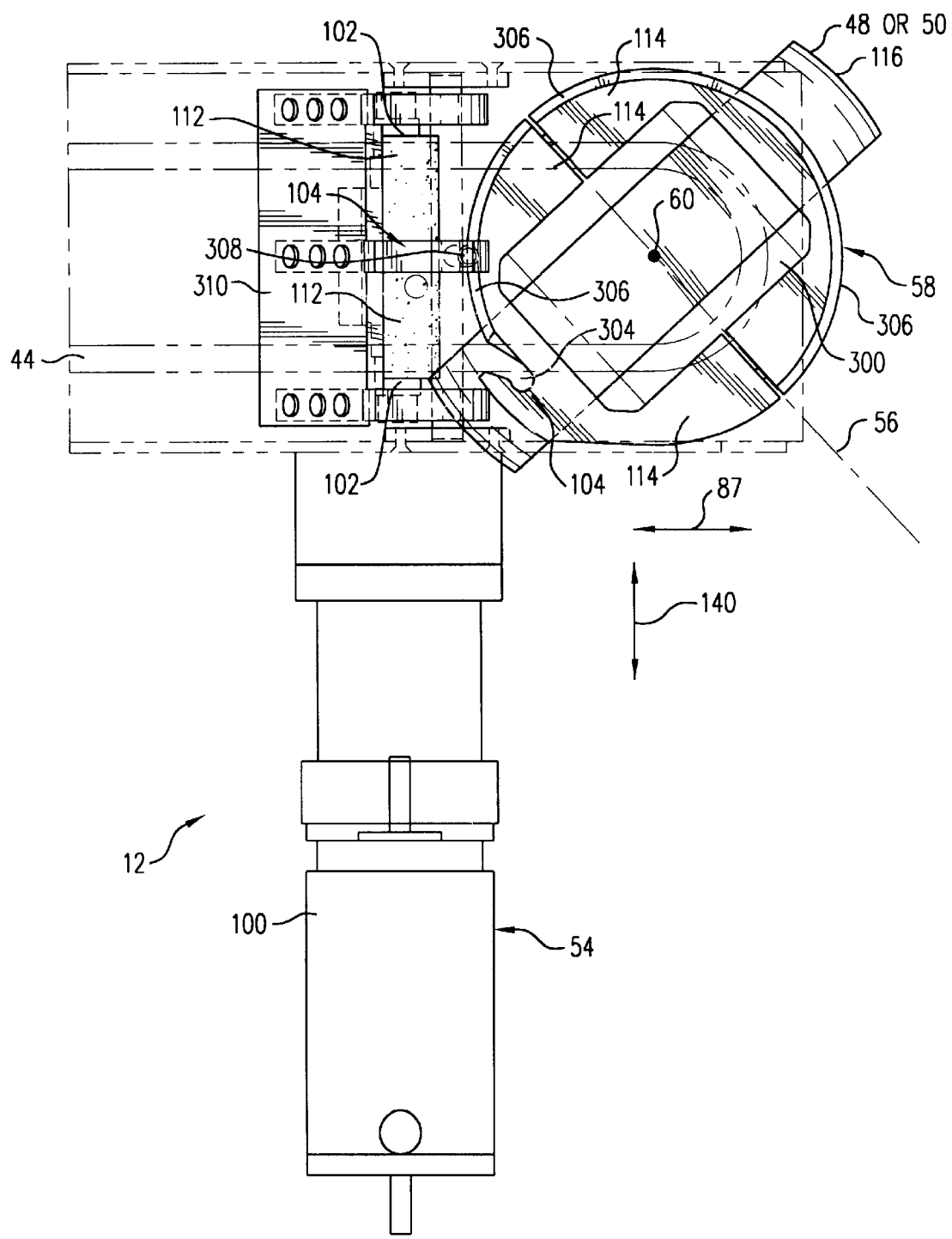

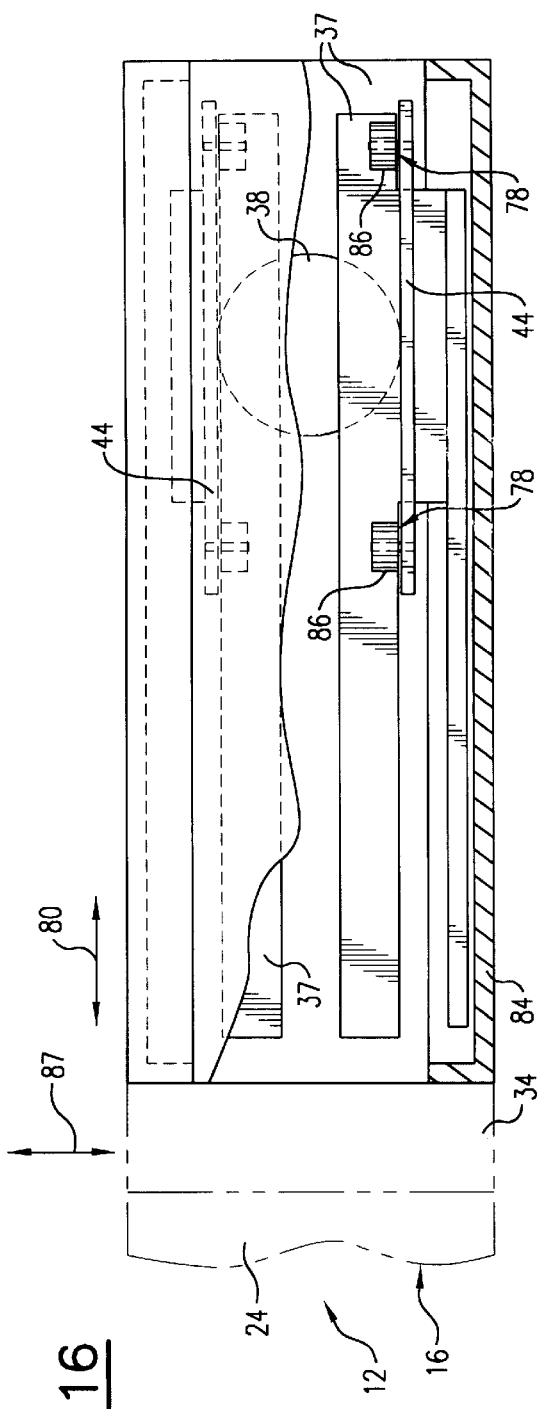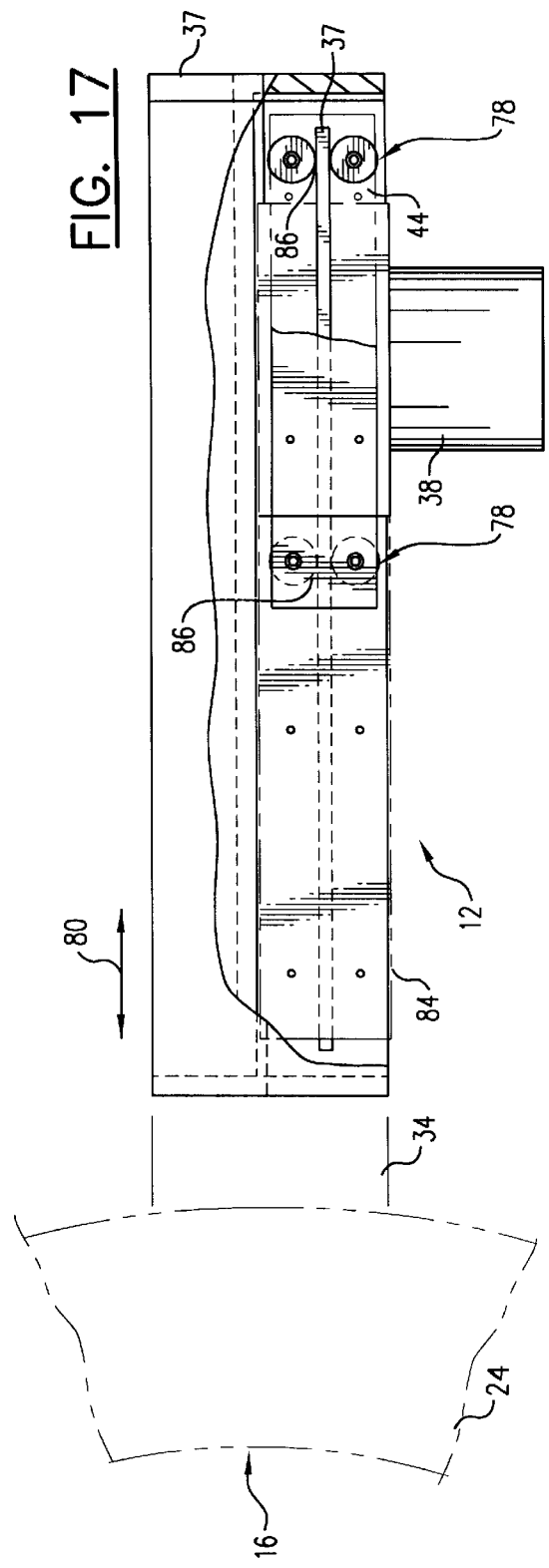

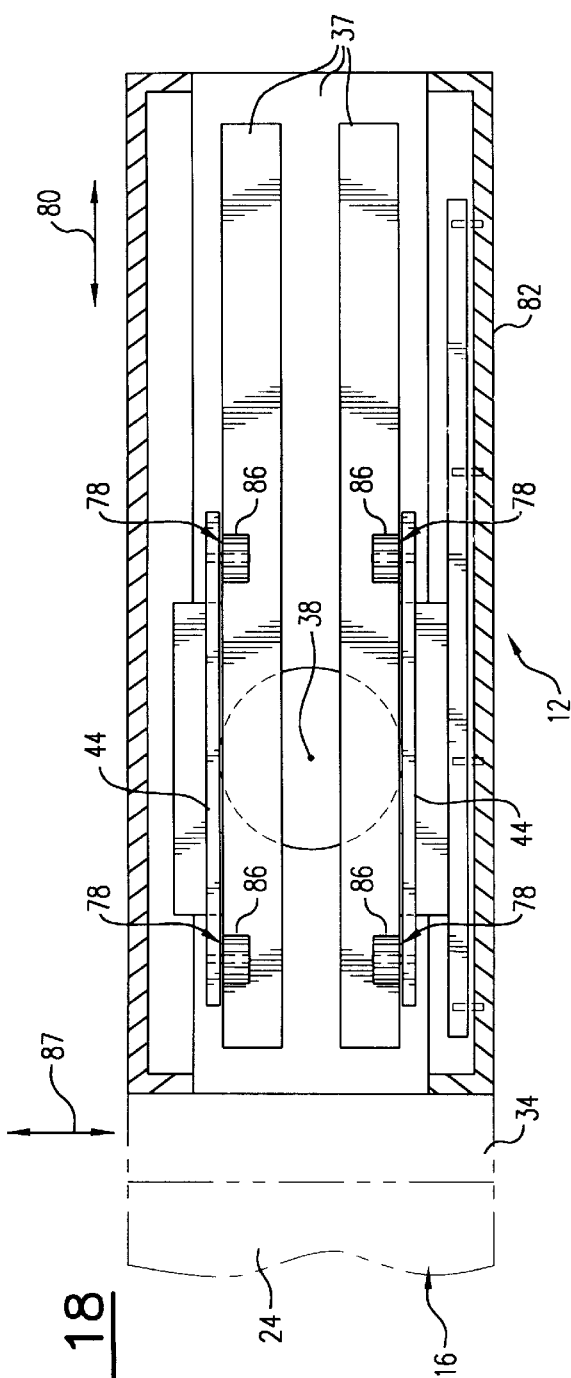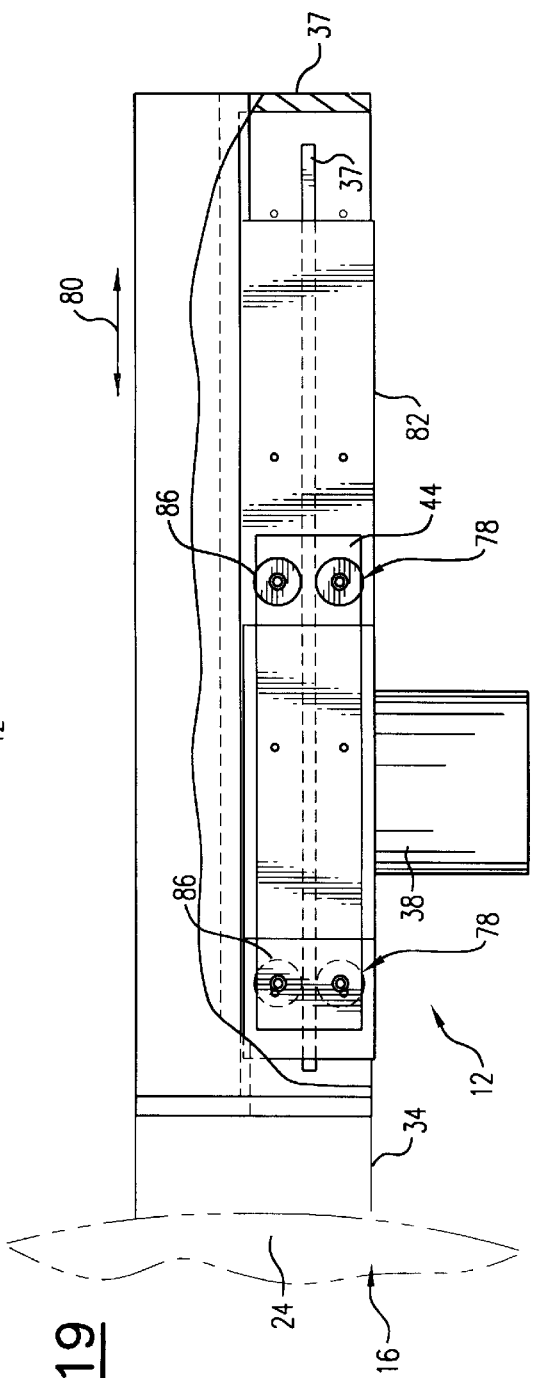

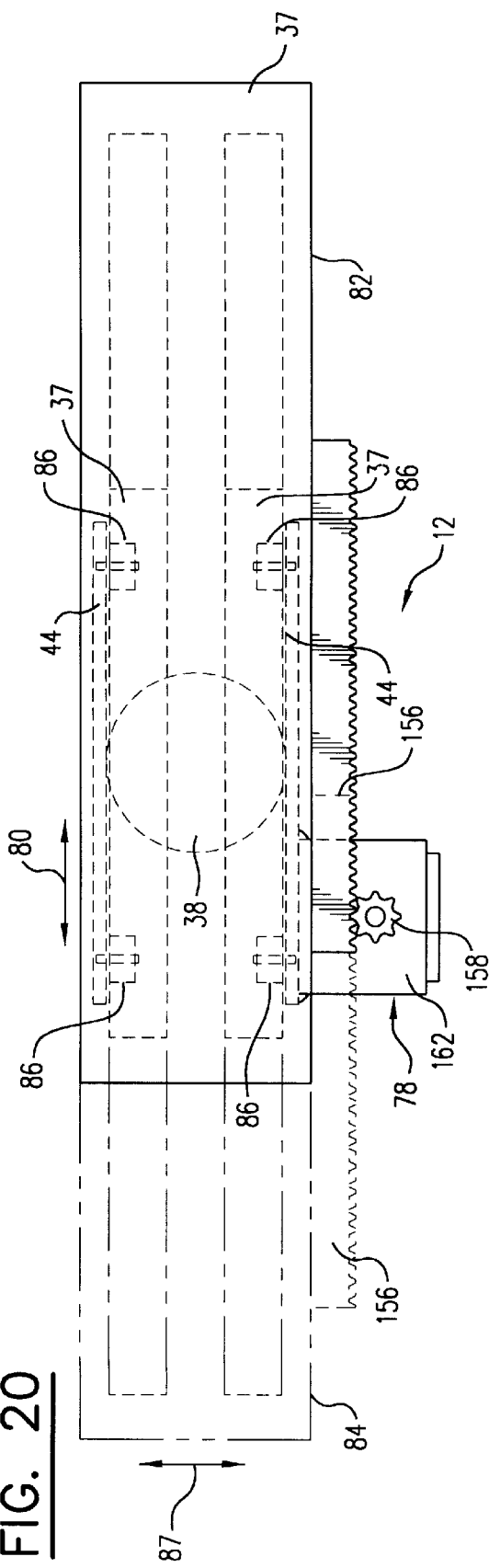
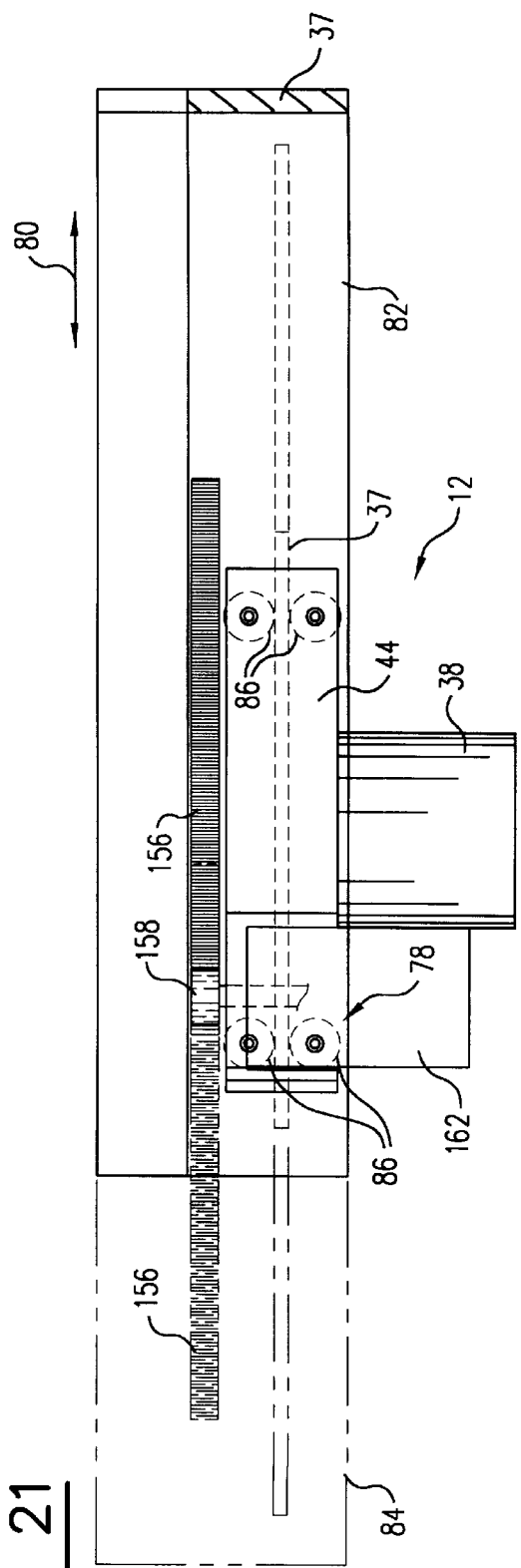

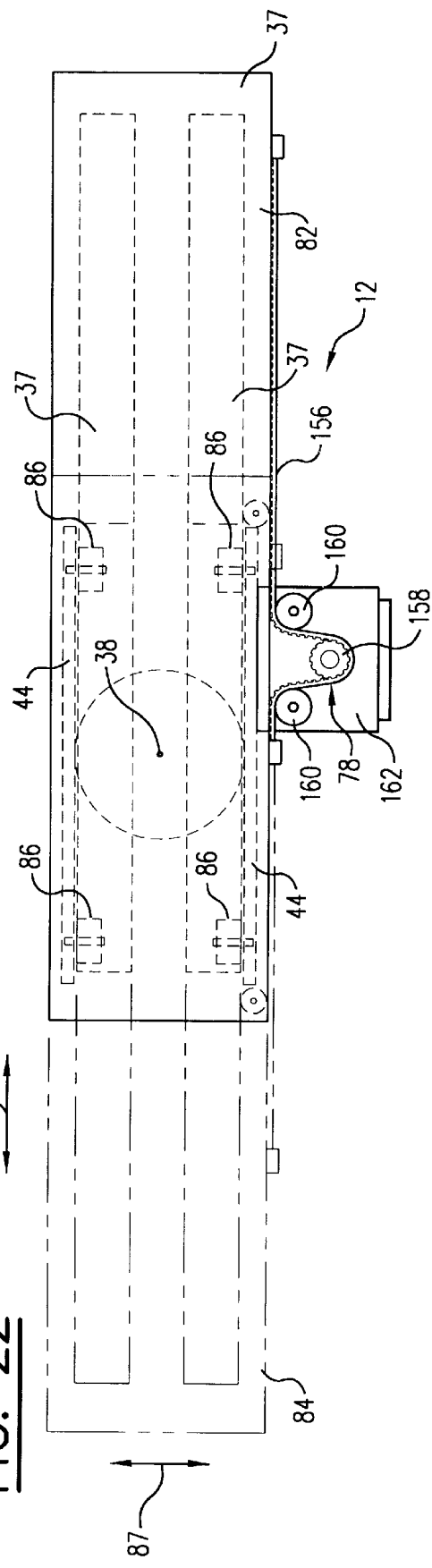
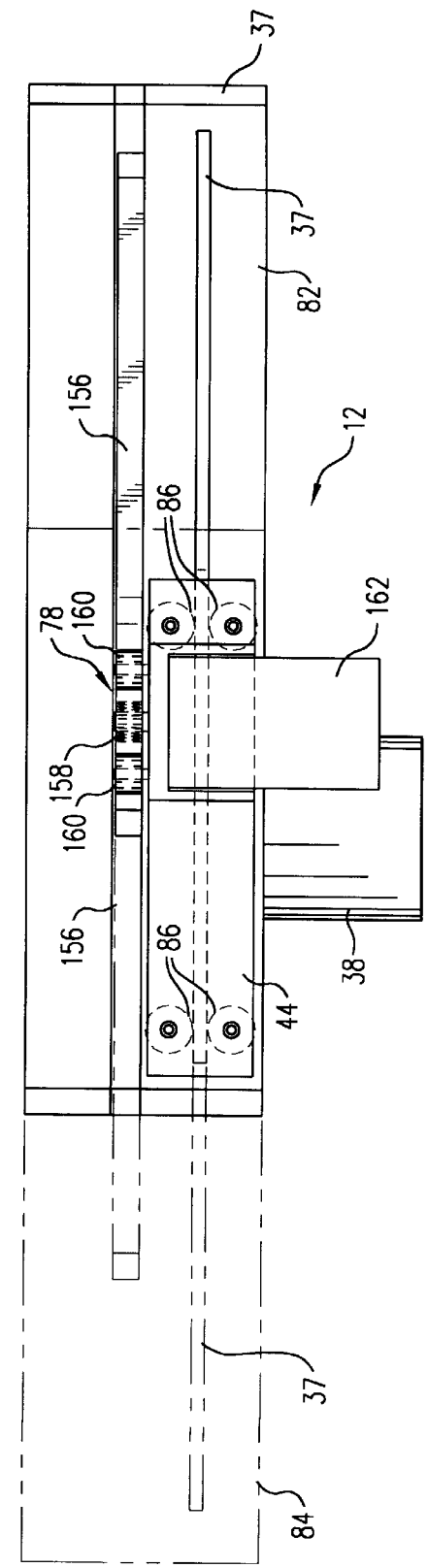

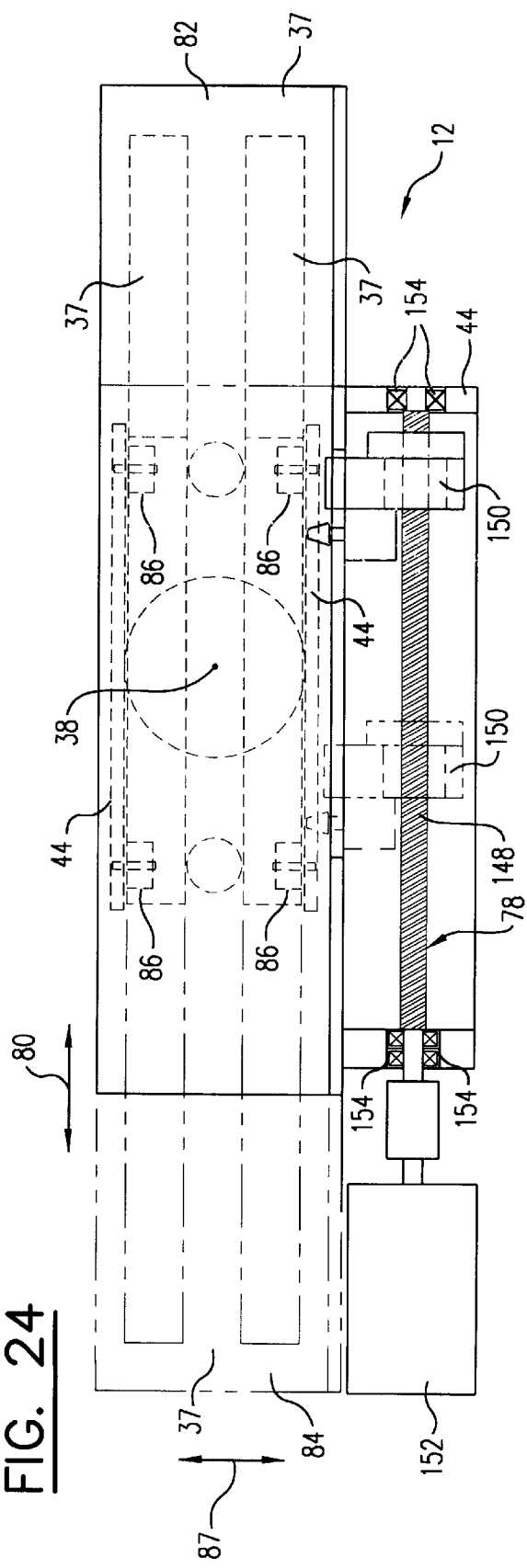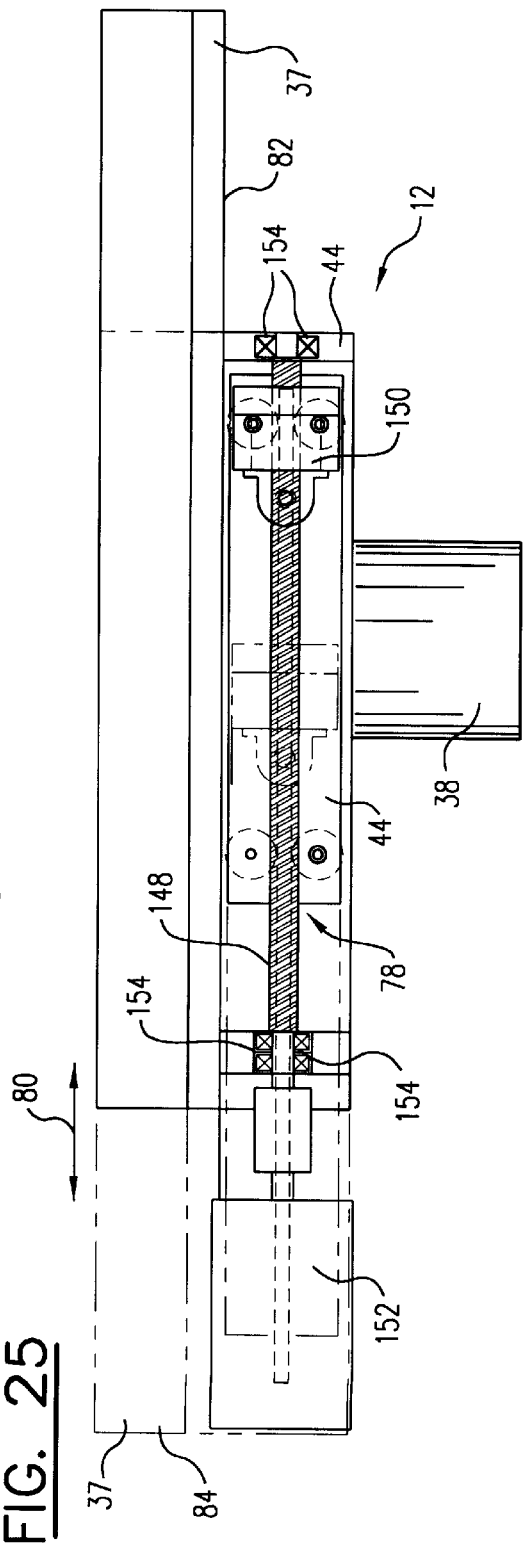

MOTORIZED SUPPORT FOR IMAGING MEANS AND METHODS OF MANUFACTURE AND USE THEREOF

CROSS REFERENCE TO RELATED APPLICATION

This is a continuation-in-part (CIP) application of a commonly owned, copending patent application, titled "Motorized Support For Imaging Means And Methods Of Manufacture And Use Thereof", Ser. No. 09/087,393, which was filed in the United States Patent and Trademark Office on May 29, 1998. The Specification and drawings of the earlier patent application are incorporated herein by this reference.

COPYRIGHT NOTICE

® Copyright 1999, James R. Vance. All rights reserved.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

TECHNICAL FIELD

This invention relates to motorized supports for mobile medical imaging systems and methods of manufacture and use thereof. More particularly, this invention relates to improved electrically-powered, motorized, mobile support equipment having means for relatively precisely, mechanically guiding, advancing, retracting and/or propelling one or more types of medical imaging equipment about at least a portion of a body of a patient.

BACKGROUND ART

There are certain medical procedures that are typically conducted using C-arm imaging systems, such as various interventional and endovascular procedures wherein medically related images are taken of arteries, blood vessels, and devices and substances that are placed within the arteries and blood vessels of a patient.

Once the patient is properly situated on a table top, a C-arm of such medical imaging equipment is caused to pass relatively close to or sweep around the pertinent portions of the body of the patient.

Much of such medical imaging equipment or systems currently being used within modern hospitals and clinics are permanently affixed to the ceiling and/or floor of the building. One of the many disadvantages of such equipment or systems is that they require an extensive support structure. Furthermore, since such equipment or systems are permanently attached or affixed to the building, they require placement within one or more specially dedicated rooms. Permanently affixed attachment within a dedicated room dramatically limits the availability of such equipment, creates scheduling problems, and limits the types of procedures that can be done with such equipment.

Since such equipment is usually permanently attached or affixed directly to the building and require substantial support structures, the specially dedicated rooms such equipment is housed within must be extensively prepared, including such tasks as: lining the walls with lead plates; securing tracking, heavy equipment, transformers and cabling to the ceiling and floors; rewiring the room to meet the requirements of the equipment; and constructing building barriers behind which the operators of the equipment must stand. Consequently, the cost to construct such dedicated rooms is very expensive.

The time required to construct, modify and prepare such dedicated rooms and install the associated permanently mounted imaging systems is also very costly, and creates health hazards and problems within what is supposed to be a sterile environment. This is particularly true if such permanently mounted systems are installed in or near operating rooms or emergency wards.

Furthermore, such specially dedicated rooms and associated equipment generally cannot be used during the construction, modification, preparation, installation and testing phases associated with such permanently mounted equipment and systems.

Ceiling suspended systems can create additional problems within what must be a sterile environment within operating rooms. For example, debris must not fall from overhead structures and equipment or from their related and required support structures, tracks, and the like, that are often positioned directly above the patient and the operating table. Furthermore, suspended systems can cause interference with other overhead equipment and devices, such as lighting, sterile room ventilation equipment, and anesthesia devices, that are used within operating rooms.

Due to excessive costs, immobility, and the inflexibility of using such equipment within dedicated rooms, mobile or portable C-arm x-ray imaging systems were created. One example is the Philips BV212 x-ray system. Such systems were sufficiently smaller and mobile to enable the device to be pushed or pulled manually into a surgery or operating room. In other words, such devices were manually pushed or pulled around from room to room within a hospital or clinic.

Once the C-arm is placed into position along side the patient table, the imaging procedures of the blood vessels or tracking/chasing of devices within the blood vessels can be performed. During these procedures, the C-arm device is manually pushed or pulled along the length of the patient table. In most cases, multiple positioning is required in order to perform the entire procedure. For example, typically, a single image is taken with the C-arm over the chest portion of the patient. When the time arrives, a second image is taken with the C-arm repositioned over the thighs of the patient. Thereafter, the C-arm is again repositioned down to the patient's lower extremities where another imaging process is performed. Because of the size, weight, and multitude of simultaneous functions needed to be performed with the mobile C-arm device, it is very difficult and burdensome to accomplish accurate movement of such systems.

In addition, because such mobile C-arm systems are manually maneuvered, it is arduous, if not impossible, to simultaneously move the device longitudinally, transversely and vertically all at the same time, such as within an X-Y coordinate system.

Furthermore, the tracking of medical devices inserted into blood vessels requires rapid movement of the mobile C-arm device in a back and forth series. For example, the chasing or tracking of a catheter tip enters a femoral artery near groin area and then is moved up into the aorta and is moved back and forth repeatedly. This requires precise, quick movements which are extremely difficult to perform by manually maneuvering the C-arm device. This task is very cumbersome, difficult, and often impossible to accomplish using a manual system.

In summary, heretofore C-arm imaging or imaging equipment were either permanently fixed and secured to the floor and/or ceiling of a dedicated room, or consisted of mobile C-arm imaging systems that were manually pushed or pulled about a patient table and throughout the hospital. The key words here are "permanently", "fixed" and "manually."

In particular, heretofore, mobile C-arm imaging systems have not had motorized supports, carts or carriages.

There were some radiographic units, used to take a plain X-ray of a patient's body, that were attached to a minimally motorized base, cart or carriage. However, such bases, carts or carriages were motorized only to move in a limited fashion to transport such equipment down a hallway. Due to the size and weight of the equipment, the motorized bases, carts or carriages on these radiographic systems were used just to get the unit from the radiology department up to the patient's bed.

Such radiographic equipment is extremely heavy, bulky and most workers within a hospital or clinic are generally incapable of pushing such heavily weighted units. For example, some of these minimally mobile radiographic units weigh about three-hundred to eight-hundred pounds (300 to 800 lbs.) each. Due to their heavy weight, they are provided with large, imprecise, motorized wheels that simply drive the unit into an elevator or down a hallway. Such motorized wheels are not used during the performance of the medical procedures.

As may be appreciated, the manipulation of such heavy, massive and bulky equipment requires a considerable amount of space and is thus of minor utility where access and moving room is limited. Due to space requirements, operation of this type of equipment generally necessitates use within a considerably large room. Not only does the manipulation of this type of equipment require additional space, but the cumbersome size and shape of the equipment itself severely limits the utility of these devices.

Once positioned adjacent to a patient, such equipment must be manhandled into position and the wheels are locked into a stationary, nonmoving position. Due to their excessive weight, these devices are quite difficult to push.

Once such equipment is placed into position, the equipment stays put, fixed and is not moved until the procedure is completed. In other words, such equipment is not motorized when placed adjacent to a patient. If needed, either the patient or the patient table is moved if needed.

The following patents and materials describe a wide variety of different imaging machinery: Janssen et al. (U.S. Pat. No. 4,481,656, issued Nov. 6, 1984); Pajerski et al. (U.S. Pat. No. 4,697,661, issued Oct. 6, 1987); Barud (U.S. Pat. No. 4,716,581, issued Dec. 29, 1987); Louiday (U.S. Pat. No. 4,866,751, issued Sep. 12, 1989); Koropp (U.S. Pat. No. 4,868,845, issued Sep. 19, 1989); Hahn et al. (U.S. Pat. No. 4,872,192, issued Oct. 3, 1989); Van Steenburg (U.S. Pat. No. 4,912,754, issued Mar. 27, 1990); Sebring (U.S. Pat. No. 4,960,271, issued Oct. 2, 1990); Kaul et al. (U.S. Pat. No. 5,008,921, issued Apr. 16, 1991); Van Steenburg (U.S. Pat. No. 5,048,071, issued Sep. 10, 1991); Hughes (U.S. Pat. No. 5,147,002, issued Sep. 15, 1992); Sebring (U.S. Pat. No. 5,156,166, issued Oct. 20, 1992); Kraft (U.S. Pat. No. 5,350,033, issued Sep. 27, 1994); Harrawood et al. (U.S. Pat. No. 5,386,453, issued Jan. 31, 1995); Schaefer et al. (U.S. Pat. No. 5,425,068, issued Jun. 13, 1995); Pellegrino et al. (U.S. Pat. No. 5,425,069, issued Jun. 13, 1995); O'Farrell, Jr. et al. (U.S. Pat. No. 5,426,683, issued Jun. 20, 1995); Galando (U.S. Pat. No. 5,475,730, issued Dec. 12, 1995); Pellegrino et al. (U.S. Pat. No. 5,499,284, issued Mar. 12, 1996); Aoki et al. (U.S. Pat. No. 5,503,416, issued Apr. 2, 1996); Kadowaki et al. (U.S. Pat. No. 5,544,217, issued Aug. 6, 1996); Hanover (U.S. Pat. No. 5,583,909, issued Dec. 10, 1996); Tanaka (Japan Patent No. 3-251,230(A), issued Nov. 8, 1991); and Philips brochure titled "BV212, Broaden your vision" (date of publication unknown).

The primary problems with the aforementioned systems include the requirements and limitations that: (a) a specially constructed or renovated and extremely expensive room be built to house such equipment; (b) such room must be dedicated solely to use with such equipment; (c) such equipment is inappropriate for use within a sterile environment of an operating room; (d) a patient must be transported to the equipment; (e) alternatively, such heavy and bulky mobile equipment must be manually pushed or pulled through a crowded hallway or corridor; (f) such heavy and bulky minimally mobile equipment must be manually pushed, manipulated, positioned, repositioned and then removed from a traditionally very small operating room; (g) use of such heretofore known devices is extremely time consuming because the device must be manually moved and repeatedly repositioned; (h) use of such devices sometimes results in excessive exposure to x-rays along a patient's body and excessive contrast agents being injected into the patient's body; and/or (i) such mobile systems cannot perform multiple tasks simultaneously. Heretofore, such mobile systems had a very limited ability or difficulty to: scan from the patient's head to the patient's toes; track devices within the patient's body; and stay in unison with the surgeon's desired location during the procedure.

The results of these drawbacks and limitations have far reaching effects in terms of: (a) increasing the cost to construct and maintain special facilities to house such equipment; (b) jeopardizing the safety of patients by prolonging the procedure, exposing the patient to additional x-rays, and increasing the amount of contrast agents; (c) creating a difficult environment within which these medical procedures are conducted due to the need to manually push and pull the heavy and bulky equipment; (d) requiring the attention of specially skilled individuals to manhandle and operate such equipment; and (e) obtaining less than optimal results from the crude, inaccurate and inexact methods currently used to position such equipment, all of which significantly increase the cost to perform these medical procedures.

It is also extremely ill-advised to move the patient during such procedures by using a floating table top.

It is firmly believed that the above-listed patents and information, whether taken alone or in combination, neither anticipate nor render obvious the current invention. The foregoing explanation does not constitute an admission that such disclosures or information are relevant or material to the appended Claims. Rather, such disclosures and information relate only to the general field of the current invention and constitute the closest art of which the inventor is aware.

DISCLOSURE OF INVENTION

The current invention overcomes most all of the above-identified disadvantages and provides numerous advantages heretofore unavailable within the medical profession.

Heretofore, most scanning and imaging equipment were required to be permanently placed within a special room. This invention now permits such equipment to be used in a mobile manner and is not fixed to the ceiling or floor.

Most notably, this invention provides doctors, surgeons and medical technicians with a mobile scanning and/or imaging apparatus that can be wheeled into a room of relatively confined space to conduct a progressive and continual scan of a patient's body, without having to move the patient or manually reposition the apparatus during the procedure. For example, this invention can be used with a mobile C-arm x-ray imaging system for conducting a continuous imaging of blood vessels from the aorta and progressively sweep down the patient's body. This invention could also be used to track devices within blood vessels in an automated and more detailed and specialized manner. The apparatus moves while the patient remains stationary.

This invention allows the procedures to be performed in a faster, easier and more efficient manner with less complications to both the patient and the operator. Furthermore, since less time is required to operate and manipulate the imaging equipment, the patient no longer needs to be exposed to excessive doses of radiation or other materials. Therefore, this invention is safer for patients to use that the devices heretofore known in the art.

The apparatus of this invention provides an easily actuated, self-propelled, precision propulsion means for mechanically guiding, advancing and retracting medical scanning and/or imaging means about the body of the patient. The apparatus may be actuated via a remote control device, a radio control device, a body mounted control device, or any other desired device and/or placement.

The current invention includes an apparatus that basically defines a motorized cart, carriage or support base upon which a piece of mobile medical scanning and/or imaging equipment is operatively attached, secured, transported and operated. The apparatus has a plurality of wheels that can be either totally motorized or switch back and forth between being motorized and manually manipulated.

Within the preferred embodiment of this invention, the apparatus has: (a) a lower chassis, undercarriage, cabinet, frame or housing which permits support for a C-arm and/or imaging equipment and movement or propulsion of the apparatus along a floor; and (b) an upper chassis or extension arm operatively and movably secured to the lower chassis. The lower chassis is positioned above a floor for moving medical scanning equipment about a portion of a body of a patient. The upper chassis or extension arm is operatively secured or attached to the lower chassis and supports and moves the C-arm and/or imaging equipment in a cantilevered manner between a retracted or shortened position and a projected, extended or lengthened position.

More particularly, the lower chassis is supported upon the floor by use of a first drive wheel, a second drive wheel and a rotatable, omnidirectional third wheel. Of course, addition wheels could be used, if desired. The first drive wheel, the second drive wheel and the third wheel are each operatively secured, attached or connected to the lower chassis and are arranged beneath the lower chassis in such a manner as to provide support, stability and means for moving or propelling the lower chassis across or relative to the floor. For example, the first drive wheel, second drive wheel and the third wheel may form three respective corners of a generally large triangle beneath the lower chassis. In other words, the first drive wheel, the second drive wheel and the omnidirectional third wheel form a three-point or tripod support for the C-arm, scanning and/or imaging equipment.

Preferably, the first drive wheel and the second drive wheel are secured to the lower chassis in such a manner that they can be positioned to have a co-linear and/or parallel orientation one to another.

The first drive wheel should be capable of being rotated about a first generally horizontal axis and a first generally vertical axis. Similarly, the second drive wheel should be capable of being rotated about a second generally horizontal axis and a second generally vertical axis.

Within the preferred embodiment of this invention, the third wheel is rotatable in an omnidirectional manner and is a non-driven wheel. In essence, the third wheel permits movement of that portion of the lower chassis in nearly any direction which is generally parallel to or horizontal with the floor. Of course, additional non-driven wheels could also be used, if desired.

Alternatively, the third wheel could be a third drive wheel with an associated drive mechanism.

However, for reasons of simplicity, a non-driven third wheel is used within the preferred embodiment of this invention. For example, if desired, the third wheel may comprise a spherical ball that is retained within an appropriate housing or receptacle.

This invention may include means for selectively rotating the first drive wheel about the first vertical axis between a first traveling position and a first operational position. The first traveling position is generally tangential or perpendicular to the first operational position.

Similarly, means may be provided for selectively rotating the second drive wheel about the second vertical axis between a second traveling position and a second operational position. The second traveling position is generally tangential or perpendicular to the second operational position.

Within the preferred embodiment of this invention, such vertical axis rotating means are generally defined by respective first and second drive wheel engagement mechanisms.

The first drive wheel engagement mechanism is secured to the lower chassis and includes a first generally-vertical axle, shaft or rod which defines the first generally-vertical axis. The first generally-vertical axle is operatively secured to a first U-shaped wheel support, bracket or coupling, which in turn is operatively secured to a first generally-horizontal axle, shaft or rod that defines the first generally-horizontal axis. The first drive wheel is operatively secured to the first generally-horizontal axle. Thus secured, the first drive wheel can be selectively pivoted between the first traveling position and the first operational position.

The first drive wheel engagement mechanism also includes a rotatable first cam that generally surrounds the first U-shaped wheel support and/or first generally-vertical axle. Rotation of the first drive wheel and associated first cam permits the first drive wheel to be operatively locked into engagement with a first drive means or be disengaged therefrom.

Similarly, the second drive wheel engagement mechanism is secured to the lower chassis and includes a second generally-vertical axle, shaft or rod which defines the second generally-vertical axis. The second generally-vertical axle is operatively secured to a second U-shaped wheel support, bracket or coupling, which in turn is operatively secured to a second generally-horizontal axle, shaft or rod that defines the second generally-horizontal axis. The second drive wheel is operatively secured to the second generally-horizontal axle. Thus secured, the second drive wheel can be selectively pivoted between the second traveling position and the second operational position.

The second drive wheel engagement mechanism also includes a rotatable second cam that generally surrounds the second U-shaped wheel support and/or the second generally-vertical axle. Rotation of the second drive wheel and associated second cam permits the second drive wheel to be operatively locked into engagement with a second drive means or be disengaged therefrom.

Within the preferred embodiment of this invention, the first drive wheel and the second drive wheel are each manually moved between their respective traveling and operational positions. Alternatively, a motor driven mechanism and/or solenoid could be provided to rotate the first drive wheel and/or second drive wheel between such two positions.

When the first and second drive wheel engagement mechanisms are moved to their respective disengaged positions, the first and second drive wheels can be activated or rotated to move along a common or independent travel path. For example the first and second drive wheels may be freely rotatable about their respective first and second vertical axises. Alternatively, the first and second drive wheels may be fixed so that they travel parallel to one another and do not rotate about their respective first and second vertical axises.

Within the preferred embodiment of this invention, the drive wheels are disengaged from the powered drive motors and are not powered when placed and secured within their transporting positions. In other words, the drive wheels are disengaged from the drive motors and are not powered when in their transporting positions. To accomplish this task, an engagable and disengagable clutch mechanism or cam mechanism with related locking pins may be operatively placed between each drive wheel and their respective drive motors.

Alternatively, the drive wheels can be powered when placed and secured within their transporting position.

When the first and second drive wheel engagement mechanisms are moved to their respective locked and engaged positions, the first and second drive wheels can be activated or rotated to move along a common operation path.

In order to obtain movement or propulsion of the lower chassis, means are provided for mechanically or electrically rotating the first drive wheel about the first generally-horizontal axis. Similarly, means are provided for mechanically or electrically rotating the second drive wheel about the second generally-horizontal axis in a selectively controlled manner.

In other words, the means for rotating the first and second drive wheels about their respective horizontal axes may be defined by one or more drive wheel rotation mechanisms that can only be activated when the drive wheels are moved from their respective disengaged positions to their locked or engaged operational positions.

For example, the first drive wheel can be selectively and operatively secured, attached or coupled to a mechanically or electrically powered first drive motor. Similarly, the second drive wheel can be selectively and operatively secured, attached or coupled to a mechanically or electrically powered second drive motor.

If desired, the first drive wheel and the second drive wheel may be operatively connected to their respective first and second drive motors via a direct in-line connection or through the use of a single or plurality of gear drives, belts, pulleys, and/or timing belts and related caster timing pulleys. Alternatively, the drive motors may be operatively connected to their respective drive wheels via a single or plurality of ninety degree or other type of gear drives.

If desired, each drive motor may be provided with a clutch mechanism. When the clutch mechanisms are deactivated or disengaged, there is no operable connection between the drive motors and the drive wheels. Instead, the apparatus can simply be pushed for transportation. When the clutch mechanisms are engaged, the drive wheels can be rotated by one or more drive motors.

The first drive motor and the second drive motor are each and both operatively secured to the lower chassis.

Any drive motor or other motor used within this invention could comprise a linear motor or servo-drive motor with or without its associated electronic gearing and electronic line shafting.

Within the preferred embodiment of this invention, the first drive wheel and the second drive wheel generally comprise heavy-duty industrial casters that are driven by twin, independent, electric drive motors with encoders that rotate on thrust bearings.

More particularly, within the preferred embodiment of this invention, the first drive motor is provided with a rotatable first drive shaft to which a first contact wheel is rigidly or fixedly attached. When the first drive wheel is rotated to its operational position, the first cam directs the first contact wheel to be urged against and engage an exterior face or portion of the first drive wheel. Thus positioned, rotation of the first drive shaft causes the first contact wheel to rotate, which causes the first drive wheel to also rotate.

Similarly, it is preferred that the second drive motor is provided with a rotatable second drive shaft to which a second contact wheel is rigidly or fixedly attached. When the second drive wheel is rotated to its operational position, the second cam directs the second contact wheel to be urged against and engage an exterior face or portion of the second drive wheel. Thus positioned, rotation of the second drive shaft causes the second contact wheel to rotate, which causes the second drive wheel to also rotate.

When propelled, the lower chassis moves along a first path when the first drive wheel is in the first traveling position and the second drive wheel is in the second traveling position.

However, after the first drive wheel is moved or rotated to the first operational position, and the second drive wheel is moved or rotated to the second operational position, the lower chassis can be moved or propelled along a second or operational path, which is preferably generally parallel to a longitudinal length of a patient examination table.

The electronic coupling and/or activation of the independent first drive wheel and the second drive wheel can be used to control the relative rotation of one drive wheel to the other drive wheel, depending upon the direction and rate of rotation. When the operator engages the apparatus to traverse in a straight operational path or line, the drive wheels are generally coupled or activated together to rotate and move the apparatus in the same direction with an one to one (1:1) ratio, as they would be in a mechanical drive shaft coupled system.

If a direction is given to turn, the relative ratios can be electronically controlled to allow one drive wheel to essentially pivot around, outrun or fall-behind the rotation of the other drive wheel while both drive wheels remain rotating. This ratio-metric control functionality of the first drive wheel and the second drive wheel enable the operator to steer the apparatus, if desired, and align the apparatus and accompanying imaging means to the longitudinal axis of the examination table.

Alternatively, one or both of the drive wheels can be decoupled to a non-driven position. When both drive wheels are placed within a decoupled, non-driven position, the apparatus of this invention can be manually pushed down a hallway. For example, within the preferred embodiment, both drive wheels can be pulled or rotated toward each other. The apparatus can then be simply pushed down the hallway.

Although the omnidirectional third wheel could simply be a regularly gimbled wheel, within the preferred embodiment of this invention, the third wheel comprises a spherical ball which is placed within a specially designed, concave receptacle positioned within the lower chassis. For example, the third wheel could be captured and operatively held within a UHMW. This non-driven front or third wheel is mounted to the apparatus using a swivel caster type of a base which allows the third wheel to conform to nearly any desired direction of travel.

Within an alternative embodiment of this invention, the third wheel may be provided with means for actively steering the apparatus, rather than mounting the third wheel to a passive caster type of swivel base.

It is important to note that within this invention the apparatus is moved relative to an underlying floor. It is believed that this feature is in stark contrast to the devices heretofore known within the art, which are either permanently attached or secured to the floor or to a ceiling, or are wheeled around manually and the wheels are not motorized.

Furthermore, the powered drive wheels of this invention are an integral feature in the performance of the medical scanning and/or imaging procedure. In other words, the powered drive wheels of this invention are progressively activated and used during and/or throughout the scanning and/or imaging procedure. Such drive wheels are not simply used to move the equipment into the room and thereafter be disengaged during performance of the medical scanning procedure.

In addition to attaching mechanically or electrically powered drive motors on the underlying first drive wheel and the second drive wheel, the apparatus of this invention uses two distinct and separate chassises or carriages, namely, a lower chassis and an upper chassis. The powered or driven first drive wheel and second drive wheel, and the omnidirectional third wheel are all operatively secured to the lower chassis.

The upper chassis is placed upon and is operatively secured, attached or affixed to the lower chassis in such a manner that they can act and operate in unison. However, the upper chassis can be moved independently from a retracted position to an extended position relative to the lower chassis. In other words, the length or extension of the apparatus can be lengthened or contracted in an overlapping or telescopic manner by having the upper chassis move away from or toward a superimposed position generally above or relative to the lower chassis.

A portion of the upper chassis extends outwardly or is cantilevered away from the lower chassis. It is upon this extended portion of the upper chassis that the C-arm, scanning and/or imaging equipment is at least partially and operatively supported, attached and/or secured. Consequently, when the upper chassis is moved to an extended position, the attached or overlying C-arm, scanning and/or imaging equipment is similarly moved in the same direction as the upper chassis, thereby permitting such equipment to be extended toward or be drawn away from a patient laying upon the examination table.

During performance of the medical procedure, the extension and retraction movement of the upper chassis is generally tangential or perpendicular to the movement of the lower chassis, as seen within a horizontal plane.

Even though the upper chassis and the attached C-arm, scanning and/or imaging equipment can be moved and cantilevered away from the lower chassis, the center of gravity of the apparatus and of the scanning and/or imaging equipment should remain safely between the third wheel, the first drive wheel and the second drive wheel. In other words, the center of gravity of the apparatus should always be positioned at a safe distance behind the third wheel which is retained within the lower chassis. Consequently, there is no danger that the apparatus could tip over onto a patient.

The balanced structure of this apparatus and the relatively narrow, outwardly-projecting, leading leg of the lower chassis, which contains and houses the third wheel, provides a wide opening to offer a relatively open work space that permits a doctor or technician to be close to the patient when this invention is used. The structure of this invention also allows nearly unrestricted access and effortless movement into any imaging position about the patient.

In order to accomplish these tasks, the apparatus of this invention is also provided with means for mechanically or electrically moving the upper chassis in a selective and controlled manner along a predetermined third path relative to the lower chassis between a retracted position and an extended position. For example, such moving means may comprise a drive mechanism for the upper chassis or extension arm.

Within the preferred embodiment of this invention, the drive mechanism for the upper chassis includes a mechanical or electric drive unit which is attached or secured between the upper chassis and the lower chassis.

For example, when activated, the drive unit may be used to rotate a worm screw or lead screw that is supported within a bearing and ball nut which is fixed to a frame and/or to either the upper or lower chassis. Rotation of the worm screw forces the upper chassis and the overlying C-arm scanner towards the patient or away from the patient, depending the direction of rotation of the worm screw.

There are different ways of securing the worm screw and associated machinery to the apparatus. For example, the worm screw of the drive unit can be rotatably and operatively secured to the lower chassis. Then, the bearing and ball nut is operatively secured to the upper chassis.

Alternatively, the worm screw of the drive unit can be rotatably and operatively secured to the upper chassis, and the bearing and ball nut can be operatively secured to the lower chassis.

The drive unit may simply comprise a linear motor and associated reduction and/or connection gears.

The drive unit can be positioned at or near a back or rear of the apparatus. The drive unit could be positioned near or adjacent to a midsection or mid-distance between the extended and retracted positions. Of course, the drive unit could just as easily be placed at any other position along the length of the worm screw. Even though the position of the electric drive unit may be different within various embodiments of this invention, the concepts taught herein are generally the same.

Alternatively, a rack and pinion system could be used instead of a worm screw. In other words, movement of the upper chassis relative to the lower chassis, either toward or away from the lower chassis and the patient, may be accomplished and controlled by using a rack and pinion system and related, powered drive motor. For example, a shafted motor may be operatively secured to a frame and/or to either the upper or lower chassis. At least one pinion is secured or attached to the shaft of the drive motor or to an associate gear box. The pinion is positioned to engage a corresponding gear rack which is mounted to and/or placed within or adjacent to a V-track. The track is secured to, attached to or formed integrally within either the frame, upper chassis or lower chassis. As the shaft of this drive motor is rotated, the attached pinion engages the gear rack and forces the rack to move relative to the drive motor. This in turn causes the upper chassis to move relative to the lower chassis, to either extend or retract the C-arm or imaging equipment secured thereto toward or away from the patient.

Alternatively, one or more ball rails could be used. In essence, the relative movement of the upper chassis relative the lower chassis defines an indexing table.

The apparatus is also provided with a control mechanism which permits the selective and controlled activation and/or movement of the first drive wheel, the second drive wheel and the means for moving the upper carriage relative to the lower carriage. The control mechanism is controlled or operated by using a keyboard, joystick, switch pad, pendant, body mounted control device, remotely controlled device, radio controlled device, voice activated device and/or infrared control device.

Within the preferred embodiment of this invention, the control mechanism or device comprises a hand-held joystick which is operatively secured to the lower chassis and associated internal machinery via one or more cables to control the activation and movement of the first and second drive wheels and the drive mechanism on the upper chassis.

The control mechanism is preferably hand-held by an operator. Multiple operations can be easily performed by simple manipulation and/or movement of the control mechanism.

The hand-held control mechanism or control unit should have a reference point thereon so that the operator can tell in which direction the apparatus will be moving when activated. For example, within the preferred embodiment of this invention, the control mechanism comprises a lower housing having a flat surface thereon. The control mechanism is held by the operator so that the flat surface always assumes the same position relative to the operator's hands. This lower housing is held within one of the operator's hands. A joystick placed on top of the control mechanism can then be manipulated and moved by the fingers or palm of the operator's other hand. Thus constructed, the control panel enables the operator to move the joystick and thereby move the scanning or imaging equipment forward, backward, to the left side, to the right side, up and down, and/or to tilt or rotate the imaging equipment along the C-arm path. There is also an on/off switch for the apparatus.

More particularly, the control mechanism may be used activate and/or deactivate: (a) the means for rotating the first drive wheel about the first horizontal axis and thereby move the lower chassis along the second path; (b) the means for rotating the second drive wheel about the second horizontal axis to move the lower chassis along the second path; (c) the means for moving the upper chassis in a selective and controlled manner along a predetermined third path relative to the lower chassis between a retracted position and an extended position; (d) means for raising or lowering the C-arm or imaging equipment relative to the floor and lower chassis; (e) the rotation or pivotal movement of the C-arm relative to the floor; and/or (f) the imaging equipment.

The control mechanism or panel can be connected to the housing with a cord or be radio controlled so that the operator can walk down the hall, sit on the other side of the room or behind a wall during operation of the apparatus. This permits remote activation of the scanner to protect the operator from excessive x-ray radiation. Furthermore, the scanning equipment can be brought via remote control into an operating room with the C-arm covered with sterile drapes, without touching the C-arm, and then can be moved or driven out once the procedure is completed.

Alternatively, the control panel may comprise an optical and/or radio controlled lift-out unit with a receiving receptacle positioned or molded into the housing of the cabinet. If remote control is required or desired, the control panel could be lifted out of its receptacle.

The control mechanism may also have means thereon to assure that the apparatus will not move in an unpredicted manner when deactivated.

The apparatus may also be provided with programmable hardware and/or software that will shorten the time to train operators to use the apparatus and/or reduce procedure time.

Within the preferred embodiment of this invention, a cabinet or cowling is operatively mounted to the lower chassis. The cabinet of the lower chassis generally defines an enclosure within which, if desired, a portion or all of the interior machinery of the apparatus may be housed.

Preferably, the cabinet is provided with at least one handle or railing that can be used to steer and push or pull the device down a corridor or hallway when the first drive wheel and the second drive wheel are disengaged or decoupled from their respective drive motors. In essence, the handle enables the apparatus to be pushed down the hallway and when the apparatus is placed in a proper position, the first and second drive wheels can be rotated and engage their respective drive motors for selective and controlled rotation and operation of the imaging procedure. In other words, the handle can be used to steer, drive or manually push the apparatus when it is being transported down a hallway.

Handle grips may be positioned with the controls.

If desired, the control panel may be placed within the handle or railing of the cabinet, with the control buttons being placed on the inside of the handle or railing.

As introduced above, additional mobility can be provided. For example, this invention can be used to support and move a mobile C-arm x-ray device having a support column that can be used to raise or lower the imaging equipment. A lower end of the support column is attached to the lower chassis. The cantilevered upper chassis can be operatively secured or attached to an upper end of the support column. In turn, a curved guide means or support arm which hold and supports the C-arm can be secured to the terminal or cantilevered end of the upper chassis. By raising and lowering the support column, the doctor, surgeon and/or technician can easily raise or lower the C-arm.

The x-ray electronics may be placed in the cabinet or be placed within a separate support module that is also on wheels and is brought into the room with the apparatus of this invention and the associated scanning equipment.

The C-arm scanner does not pivot in a conventional manner. Rather, the cantilevered, curved guide means is provided with means for moving the C-arm through a predetermined arcuate path which generally matches the arch of the C-arm. The remaining movement of the C-arm is left to the support column, the underlying first drive wheel, the underlying second drive wheel, and the means for moving the upper chassis relative to the lower chassis.

When x-ray equipment is used, at the terminal ends of the C-arm are placed an x-ray transmitter and an x-ray receiver, respectively.

During use of the preferred embodiment of this invention, the apparatus can be manually pushed or mechanically driven down a corridor or hallway and into a room of a hospital or clinic to where the patient is laying upon an examination table. As the apparatus approaches the patient and is within the general operable vicinity of the patient, the drive wheel mechanisms may be turned to an operational position and be selectively activated. During use of the scanning and/or imaging equipment, the first drive wheel and the second drive wheel have a common, in-line orientation one with another.

Once engaged, the drive wheel mechanisms mechanically propel the apparatus along what is referred to herein as an X-axis. It is intended that the patient be laying upon an examination or treatment table, bed or platform that has a longitudinal axis that is generally parallel to the aforesaid X-axis. As the scanning and imaging procedure is conducted, the drive wheel mechanisms are activated to move the apparatus and associated scanning and/or imaging means back and forth along the X-axis, which is generally parallel to the longitudinal axis of the table, bed or platform.

The worm screw drive, the rack and pinion system, or the belt driven system can be selectively activated to cause the upper chassis and associated scanner to move in a direction that is generally tangential, perpendicular, or at right angles to the X-axis. We will refer to the movement of the upper chassis relative to the lower chassis as causing the scanner to move within a movable or repositionable Y-axis. In other words, the Y-axis can be moved along the X axis but will remain at a predictable or predetermined tangential, perpendicular, or right angle thereto.

Within the preferred embodiment of this invention, the Y-axis will generally remain at about a ninety degree (90°) angle relative to the X-axis. The X-axis and the Y-axis both generally fall within a horizontal plane.

As briefly explained above, the apparatus of this invention may also have an upright post or support column that can be extended or contracted, or raised and lowered, in a generally vertical manner generally along a Z-axis. The X-axis and Y-axis are generally tangential, perpendicular, or at right angles to this generally vertical Z-axis.

Consequently, this apparatus permits movement of the scanner within an X-axis, a Y-axis, and a Z-axis. Movement of the scanner along the X-axis is generally in a horizontal plane along the length of the patient laying upon the table, bed or platform. Movement of the scanner along the Y-axis is generally in a horizontal plane either toward or away from the patient laying upon the table, bed or platform, and in a generally tangential orientation with the longitudinal length of the table and patient. Movement of the scanner along the Z-axis is generally in a vertical plane either toward or away from the patient laying upon the table, bed or platform. Furthermore, motion can occur in one, two or even all three directions at once.

Since the scanner can be easily moved anywhere within the above-stated three-dimensional coordinate system surrounding the patient, the patient need not be positioned or laying within a plane that is perfectly parallel to the foregoing coordinate system of the apparatus. Rather, the apparatus can be manipulated or moved to produce the desired scan of the patient, without moving the patient. During operation of the scanning means, the frame or carriage of this invention precludes any angular motion relative thereto. This is true because all motion and movement of the mobile carriage or lower chassis and the indexing table or upper carriage are always perpendicular with respect to each other. Also, the apparatus can perform multiple motion tasks simultaneously.

In other words, this invention provides unrestrained movement in any direction along the plane of the floor due to the absence of any restricting guides or rails that were heretofore mounted and secured to either the floor or to the ceiling. Floor and/or ceiling mounting is no longer required. Instead, this invention is fully mobile.

Once the scan is performed, the apparatus and its associated scanner can be quickly and easily removed from the room without disturbing or moving the patient.

By controlling the activation and electrical power running to either the first drive motor or to the second drive motor, but not the other, or by operating one drive motor in forward and the other in reverse, the apparatus can be easily rotated and maneuvered.

Within the preferred embodiment of this invention, when assuming their operational positions, the first drive wheel and the second drive wheel are placed or positioned collinearly along a common X-axis. Consequently, if there is a discrepancy in the rotational rates of the drive wheels or drive motors, no problems will be created because both wheels share a common path of movement along the X-axis. In other words, by placing these two drive wheel along a common ray or path, potential torsion between the drive wheel is essentially eliminated.

To transport the apparatus down a hallway, corridor or through a room, the drive wheels should be rotated so that the effective width of the apparatus can be minimized during such travel. For example, when the scanner is being wheeled down the hallway, corridor or through the room, the drive wheels can be rotated about ninety degrees (90°) from an operational or operative position to their traveling position. Once secured within their traveling positions, both drive wheels will have a similar but generally parallel path of travel. The third wheel will either lead or trail the two drive wheels.

When switching between the operational and traveling positions, rotation of the first and second drive wheels automatically remove and insert or engage and disengage a catch pin, switch, or lockable clutch mechanism. For example, such catch pin may engage or be disengaged from the first and second cams. Once the locking mechanism is disengaged, the drive wheel can be easily rotated between its operational position and its traveling position. Once the desired position is obtained, the locking mechanism can be engaged to maintain the accuracy and safety of the apparatus.

The apparatus should be protected from operating room blood, gauze and other debris laying on the floor from entering into the mechanical and electrical components. To protect the apparatus, a bottom plate or protective shield can be used to enclose and generally encapsulate the inner workings of the apparatus.

In addition, rubber, silicon, or other flexible wiper washers or boots may be used adjacent to and/or around the drive wheels and/or around the spherical third wheel to keep out the contaminants and debris from being drawn up into the apparatus. If desired, the wiper washers may rotate with the wheels. When the drive wheels rotate, the debris and contaminants are wiped off.

The preferred and several alternative embodiments of the apparatus and associated structures of this invention, and the processes for manufacture and use thereof, are further described in greater detail within the following description, Claims and drawings of this Specification. However, to avoid any possible confusion as to the scope of the current invention, each of the following sections, claim language and the drawings of this Specification in their entirety are incorporated herein by this reference.

It should also be noted that use of alternative terms throughout this disclosure should be considered as synonyms of one another and not exclusive of one another. In other words, if a list of alternative terms or words are used within this disclosure and/or within the appended Claims, use of any of such terms or words may encompass one or more or even all of the other alternative terms as well and all terms and words covered under the Doctrine Of Equivalents.

In addition to the above-identified benefits and advantages of this invention, this invention also overcomes all or nearly all of the aforementioned disadvantages and shortcomings of the devices heretofore known in the applicable art.

The foregoing and other objectives and advantages of this invention will become more readily apparent upon reading the following disclosure and referring to the attached drawings.

BRIEF DESCRIPTION OF DRAWINGS

FIG. 4B is a partial, enlarged, exploded, schematic and perspective view of a second drive wheel, a second drive wheel engagement mechanism and a second drive wheel rotation mechanism. In nearly every respect, the second drive wheel is identical to the first drive wheel, the second drive wheel engagement mechanism is identical to the first drive wheel engagement mechanism, and the second drive wheel rotation mechanism is identical to the first drive wheel rotation mechanism.

FIG. 5 is a partial, enlarged, exploded, schematic and perspective view of a portion of a drive wheel engagement cam mechanism as contained within the drive wheel engagement mechanism illustrated within FIG. 4.

FIG. 6 also illustrates a frictional contact wheel that can be urged against and engage an outer or exterior surface or face of the first or second drive wheel.

FIG. 8 is a partial, enlarged, schematic, plan view of the drive wheel engagement mechanism and the drive wheel rotation mechanism.

FIG. 9A is a partial, enlarged, schematic, cross-sectional and side elevational view of the first drive wheel engagement mechanism in a disengaged position and the first drive wheel rotation mechanism also in a disengaged position.

FIG. 9B is a partial, enlarged, schematic, cross-sectional and side elevational view of the second drive wheel engagement mechanism in a disengaged position and the second drive wheel rotation mechanism also in a disengaged position. As stated above, in nearly every respect, the second drive wheel is identical to the first drive wheel, the second drive wheel engagement mechanism is identical to the first drive wheel engagement mechanism, and the second drive wheel rotation mechanism is also identical to the first drive wheel rotation mechanism.

FIG. 10 is a partial, enlarged, schematic, plan view of the drive wheel engagement mechanism moving toward or away from an engaged position. FIG. 10 is also a partial, enlarged, schematic plan view of the drive wheel rotation mechanism moving toward or away from an engaged position.

FIG. 12 is also a partial, enlarged, schematic, plan view of the drive wheel rotation mechanism in an engaged position.

FIG. 16 is a partial, cross-sectional, schematic, plan view of the first embodiment with the extension arm in a projected, extended or lengthened position.

FIG. 17 is a partial, cross-sectional, schematic, side-elevational view of the first embodiment with the extension arm in a projected, extended or lengthened position.

FIG. 18 is a partial, cross-sectional, schematic, plan view of the first embodiment with the extension arm in a retracted or shortened position.

FIG. 19 is a partial, cross-sectional, schematic, side-elevational view of the first embodiment with the extension arm in a retracted or shortened position.

FIG. 20 is a partial, cross-sectional, schematic, plan view of a second embodiment with the extension arm illustrated by solid lines in a retracted or shortened position, and by phantom lines in a projected, extended or lengthened position.

FIG. 21 is a partial, cross-sectional, schematic, side-elevational view of the second embodiment with the extension arm illustrated by solid lines in a retracted or shortened position, and by phantom lines in a projected, extended or lengthened position.

FIG. 22 is a partial, cross-sectional, schematic, plan view of a third embodiment with the extension arm illustrated by solid lines in a retracted or shortened position, and by phantom lines in a projected, extended or lengthened position.

FIG. 23 is a partial, cross-sectional, schematic, side-elevational view of the third embodiment with the extension arm illustrated by solid lines in a retracted or shortened position, and by phantom lines in a projected, extended or lengthened position.

FIG. 24 is a partial, cross-sectional, schematic, plan view of a fourth embodiment with the extension arm illustrated by solid lines in a retracted or shortened position, and by phantom lines in a projected, extended or lengthened position.

FIG. 25 is a partial, cross-sectional, schematic, side-elevational view of the fourth embodiment with the extension arm illustrated by solid lines in a retracted or shortened position, and by phantom lines in a projected, extended or lengthened position.

Figure 1:
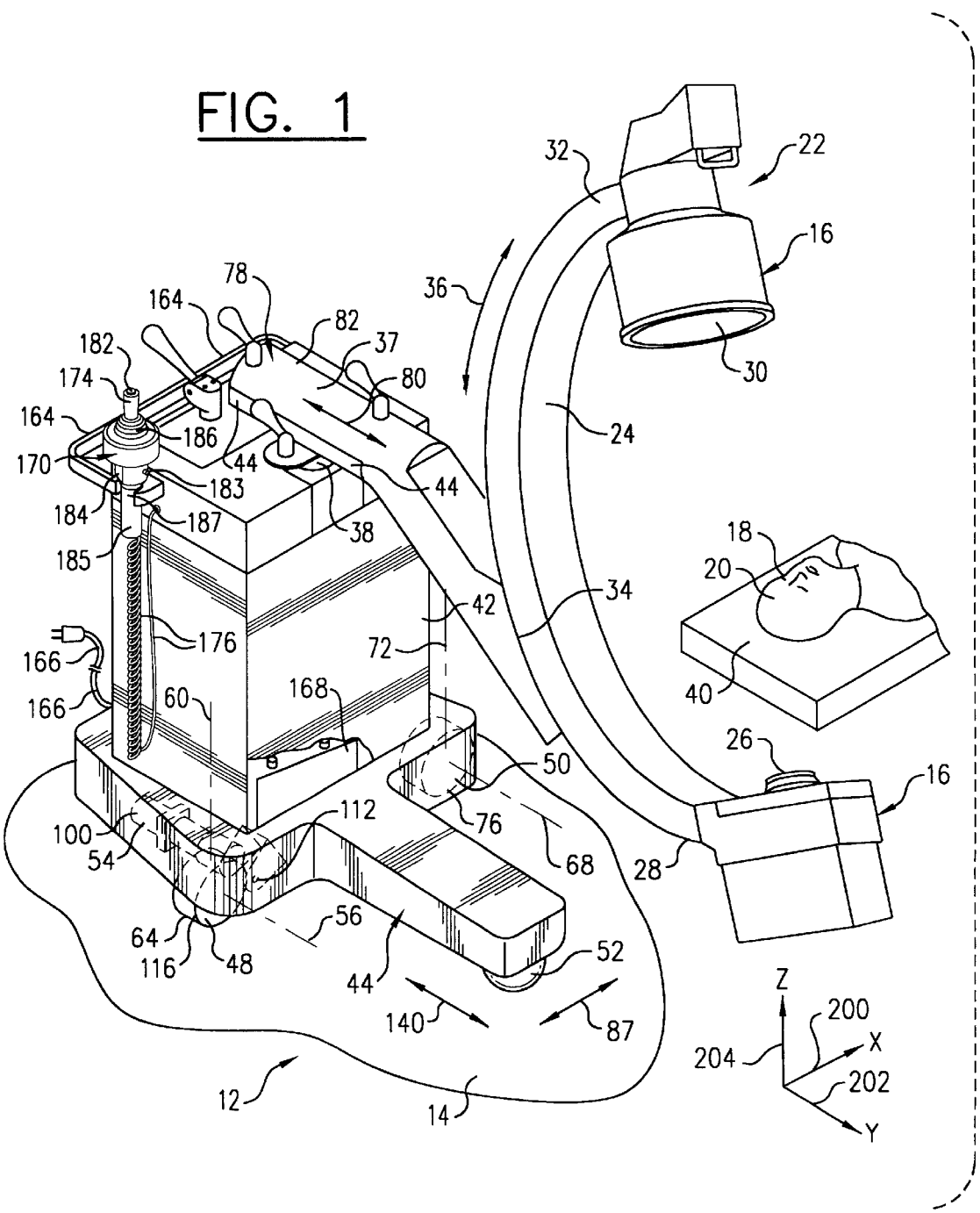
FIG. 1 is a schematic and perspective view of a first embodiment of the current invention, made in accordance with the teachings of this disclosure.

One should understand that the drawings are not necessarily to scale and the elements are sometimes illustrated by graphic symbols, phantom lines, diagrammatic representations and fragmentary views. In certain instances, details which are not necessary for an understanding of the current invention or which render other details difficult to perceive may be omitted.

BEST MODE FOR CARRYING OUT THE INVENTION

Referring to the drawings, wherein like numerals indicate like parts, the current invention includes an apparatus 12, which is placed upon and is supported by an underlying floor 14. The apparatus 12 is used to transport and control at least a portion of the operational movement of means 16 for conducting medical scans and/or images, or in other words, medical scanning equipment, about a portion of a body 18 of a patient. For example, the apparatus 12 may be used to transport and/or control the movement of mobile x-ray-imaging, angiogram, thermal-imaging, ultrasonic-imaging, magnetic-resonance-imaging, and/or any other type of medical scanning and/or imaging equipment.

The apparatus 12 is intended to significantly improve the ease and ability to gather medical data, and to dramatically increase the accuracy of such data. For example, the apparatus 12 can be used to assist in conducting: angiography, digital subtraction angiography (DSA), interventional, endovascular, catheterization, neurological, vascular, cardiac, trauma, internal, endoscopy, fluoroscopy and urology procedures; intraluminal grafting; bone studies; medical road mapping; maximal opacification; and assist in many other static and/or dynamic applications.

While conducting the medical procedure, the apparatus 12 can actively and progressively move or index the scanning and/or imaging means 16 or equipment about at least a portion of the body 18 of a patient 20 without having to manhandle the apparatus 12 to a new position to scan or register each new image. In other words, the scanning and/or imaging means 16 can be moved along at any desired speed and moved to nearly any desired location about the body 18 of the patient 20 without having to stop the medical procedure or move the patient 20. Consequently, the speed and accuracy of the data gathered are significantly higher than heretofore thought possible. Furthermore, due to the rapid gathering and high quality of such information, the fluoroscopic dose level or other tracing injections required to be given to the patient 20 can be minimized.

Within the illustrated preferred and alternative embodiments of this invention, the scanning and/or imaging means 16 or equipment generally comprises a mobile x-ray device 22 having a C-arm 24 which carries a transmitter 26 at a first end 28 thereof and a receiver 30 at an opposed second end 32.

The C-arm 24 is supported by a cantilevered, partially curved guide means 34 that is capable of guiding and advancing the scanning and/or imaging means 16, i.e., the transmitter 26 and the receiver 30, through a predetermined curved path 36.

The cantilevered, curved guide means 34 is at least partially supported by an upper chassis 37 and a support column 38 that has a generally vertical orientation. Support column 38 can be selectively raised or lowered to position, adjust and/or modify the height of the upper chassis 37 and curved guide means 34. As a consequence, the height of the scanning and/or imaging means 16 can be either raised or lowered relative to the floor 14 and relative to the patient 20.

Figure 14:
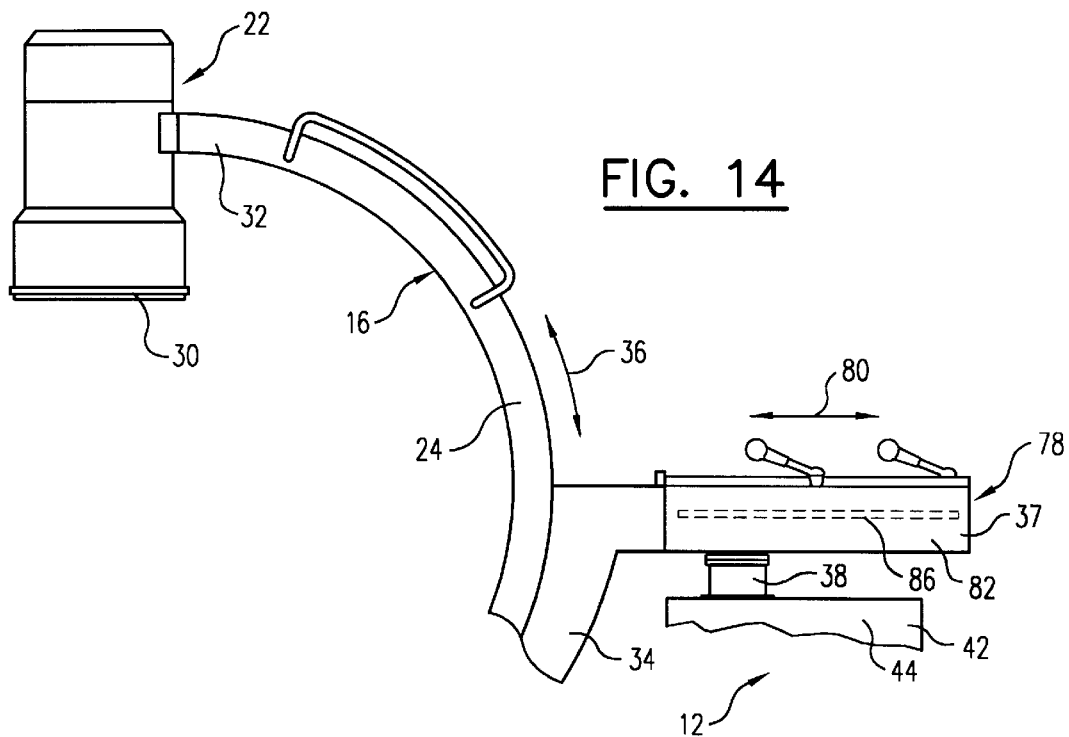
FIG. 14 is a partial, schematic and side elevational view of the first embodiment of this invention with the extension arm in a retracted or shortened position.
Figure 15:
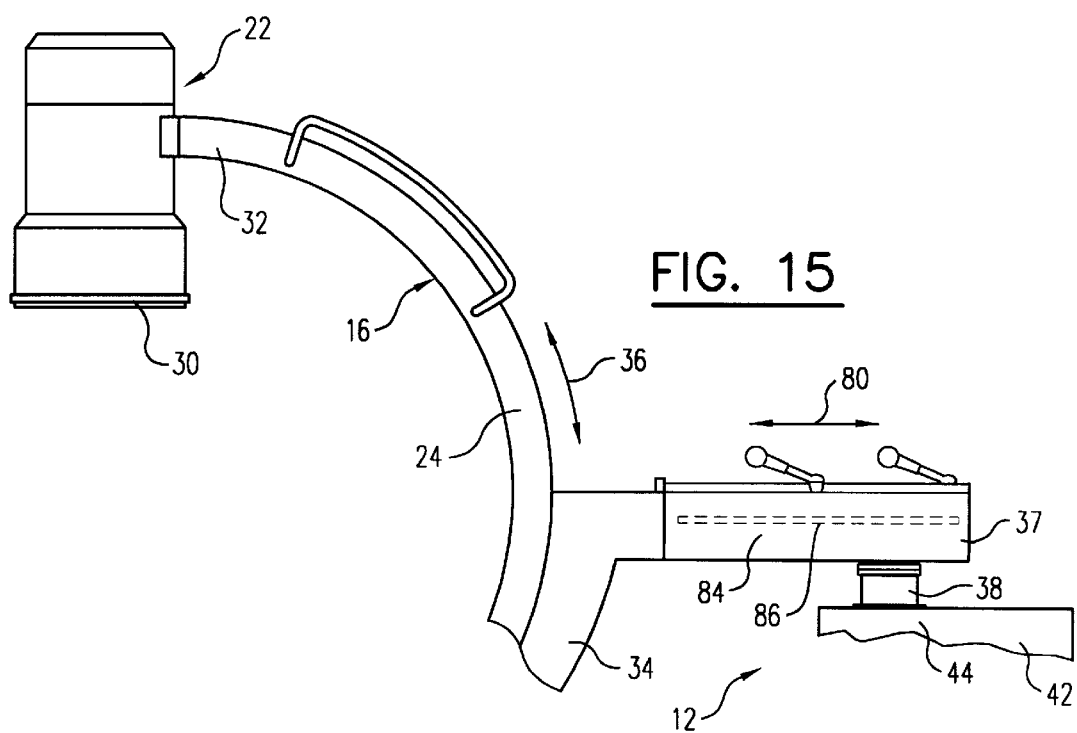
FIG. 15 is a partial, schematic and side elevational view of the first embodiment of this invention with the extension arm in a projected, extended or lengthened position.

FIGS. 1, 14 and 15 illustrate the support column 38 in a generally lowered position. FIGS. 17, 19, 21, 23 and 25 illustrate the support column 38 in a generally raised position. Of course the indicated height is not limiting in this invention. Any desired height can be achieved.

Typically, the patient 20 lays upon a transparent, translucent, radiolucent, carbon-fiber, glass and/or plastic, cantilevered table 40 which has an approximate horizontal orientation. Preferably, the table 40 is cantilevered from a fixed support structure such as from a wall, the floor 14, or a separate support stand.

Radiation emitted by the transmitter 26 of the scanning and/or imaging means 16 is permitted to pass through the table 40 and the patient 20 and be received into the receiver 30.

Electrical equipment necessary to operate and to raise and/or lower the scanning and/or imaging means 16 is preferably contained within a cabinet 42. Cabinet 42 is preferably positioned below and adjacent to the support column 38.

One scanning and/or imaging means 16 that has a C-arm 24, a transmitter 26, a receiver 30, a curved guide means 34, a support column 38 and a cabinet 42 is the BV212 mobile x-ray unit sold by Philips Medical Systems. The apparatus 12 of this invention is preferably used with such scanning and/or imaging means 16. Of course, other scanning and/or imaging means 16 or equipment could be used.

The apparatus 12 of this invention generally comprises a combination of: (a) a lower chassis 44; and (b) the upper chassis 37.

The lower chassis 44 has a first drive wheel 48, a second drive wheel 50 and an omnidirectional third wheel 52.

The lower chassis 44 has means 54 for mechanically or electrically rotating the first drive wheel 48 about a first generally horizontal axis 56 in a selectively controlled manner, and means 58 for selectively rotating the first wheel 48 about a first generally vertical axis 60 between a first traveling position 62 and a first operational position 64.

The lower chassis 44 also has means 66 for mechanically or electrically rotating the second wheel 50 about a second generally horizontal axis 68 in a selectively controlled manner, and means 70 for selectively rotating the second wheel 50 about a second generally vertical axis 72 between a second traveling position 74 and a second operational position 76.

Furthermore, the apparatus 12 includes means 78 for mechanically or electrically moving the upper chassis 37 in a selective and controlled manner along a predetermined path 80 relative to the lower chassis 44 between a retracted position 82 and an extended position 84, as best seen within FIGS. 14 and 15.

The lower chassis 44 is positioned above but adjacent to the underlying floor 14.

The upper chassis 37 can be moved relative to the lower chassis 44 between the retracted position 82 and the extended position 84. More particularly, the upper chassis 37 is operatively and movably secured to the lower chassis 44. For example, as seen within FIGS. 14 through 26, the lower chassis 44 may be provided with one or more tracks 86, grooves, slots, or indentations into which at least a portion of the upper chassis 37 is operatively and movably secured.

If desired, the tracks 86 may comprise a pair of sealed ball slide tracks, having ball rails and linear bearings that are mounted parallel to each other. The linear bearings are attached to the bottom of the upper chassis 37 allowing the upper chassis 37 to move along a plane of motion generally above the lower chassis 44.

Similarly, the tracks 86 may comprise one or more V-tracks and corresponding V-wheel slides.

Activation of the first drive wheel 48 and the second drive wheel 50 provides for motion of the apparatus 12 along the length of the examination table 40. The upper chassis 37 or indexing table is mounted in such a way as to provide motion towards and away from the side of the table 40, which is generally perpendicular to the plane of motion or path 87 of the lower chassis 44.

As best seen within FIG. 9A, the first drive wheel 48 is operatively secured to the lower chassis 44. More particularly, the apparatus 12 comprises means 88 for coupling the first wheel 48 to the lower chassis 44. The first coupling means 88 enables the first wheel 48 to rotate about the first generally horizontal axis 56 and enables the first wheel 48 to rotate about the first generally vertical axis 60.

Similarly, as best seen within FIG. 9B, the second wheel 50 is also operatively secured to the lower chassis 44. The apparatus 12 includes means 94 for coupling the second wheel 50 to the lower chassis 44. The second coupling means 94 enables the second wheel 50 to rotate about the second generally horizontal axis 68 and enables the second wheel 50 to rotate about the second generally vertical axis 72.

The first wheel 48 and the second wheel 50 are arranged to at least partially support the lower chassis 44 upon the floor 14 and enable movement of the lower chassis 44 relative to the floor 14.

The third wheel 52 is also operatively secured to the lower chassis 44. The third wheel 52 preferably comprises a rotatable and omnidirectional wheel. Consequently, the first drive wheel 48 and the second drive wheel 50 can be used to steer the apparatus 12 without the third wheel 52 dragging along or skidding against the floor 14. In other words, the third wheel 52 permits movement of the lower chassis 44 in any direction that is generally parallel to or horizontal with the floor 14.

The third wheel 52 provides additional support and stability to the apparatus 12. The third wheel is preferably supported within an elongated or outwardly extending leg of the lower chassis 44. The third wheel is position so that there will be no danger that the extension of the upper chassis 37 and/or C-arm 24 will cause the apparatus 12 to tip over due to an excessive change in the center of gravity of the apparatus 12. The center of gravity will always remain between the third wheel 52, the first drive wheel 48, and the second drive wheel 50.

In essence, the first wheel 48, the second wheel 50 and the third wheel 52 form a tripod upon which the remaining portions of the apparatus 12 are supported and upon which the apparatus 12 is moved and transported across the floor 14.

As stated above, the apparatus 12 is provided with the means 54 for mechanically or electrically rotating the first drive wheel 48 in a selectively controlled manner about the first generally horizontal axis 56. Such first rotating means 54 preferably comprises a first drive motor 100 that is secured to the lower chassis 44. The first drive motor 100 is secured to the lower chassis 44 in such a manner as to prevent rotation of a housing of the first drive motor 100 relative thereto. A drive shaft 102 of the first drive motor 100 is operatively and/or directly connected to the first drive wheel 48.

If desired, a first clutch mechanism 104 may be operatively secured between the first drive motor 100 and the first wheel 48. The first clutch mechanism 104 can be used to disengage or engage the first wheel 48 with the first drive motor 100. For example, if desired, the first wheel 48 can be disengaged from the first drive motor 100 when the apparatus 12 is being pushed down a corridor or hallway. Once the apparatus 12 is placed near to the patient 20, the first clutch mechanism 104 can be activated to engage the first wheel 48 with the first drive motor 100 for motorized operation of the apparatus 12 during the medical procedure.

The apparatus 12 should also be provided with means 66 for mechanically or electrically rotating the second wheel 50 in a selectively controlled manner about the second generally horizontal axis 68. Second rotating means 66 may comprise a second drive motor 106 that is operatively secured to the lower chassis 44.

A second drive motor 106 can be directly or indirectly connected to the second wheel 50. Of course, the second drive motor 106 would be secured to the lower chassis 44 in such a manner as to prevent rotation of a housing of the second drive motor 106 relative thereto. A drive shaft 108 of the second drive motor 106 is operatively and/or directly connected to the second wheel 50.

If desired, a second clutch mechanism 110 may be operatively secured between the second drive motor 106 and the second wheel 50. The second clutch mechanism 110 can be used to disengage or engage the second drive wheel 50 to the second drive motor 106. For example, if desired, the second drive wheel 50 can be disengaged from the second drive motor 106 when the apparatus 12 is being pushed down a corridor or hallway. Once the apparatus 12 is placed near to the patient 20, the second clutch mechanism 110 can be activated to engage the second drive wheel 50 with the second drive motor 106 for motorized operation of the apparatus 12 during the medical procedure.

If desired the first clutch mechanism 104 and the second clutch mechanism 110 can be activated or deactivated in unison, concurrently, or simultaneously.

For example, referring to FIGS. 4A, 5, 6, 7, 8, 9A, 10, 11, 12 and 13, the first drive wheel engagement mechanism and/or first clutch mechanism 104 of the preferred embodiment comprises a combination of:

(a) the first drive wheel 48;
(b) a first generally horizontal axle 56' passing through or secured to the first drive wheel 48;
(c) a first generally U-shaped wheel support 300 that at least partially surrounds the first drive wheel 48 and to which the first axle 56' is operatively secured;
(d) a first generally vertical axle 60' secured to the first U-shaped wheel support 300;
(e) a first bearing 302 and/or bearing mount secured to or incorporated within the lower chassis 44 which receives and retains the first generally vertical axle 60' and permits rotation of the first U-shaped wheel support 300 and first drive wheel 48 about the generally vertical axis 60;

(f) a rotatable first cam 114 that generally surrounds the first U-shaped wheel support 300, wherein the first cam 114 has a first locking pin receiving slot 304 and a ramped surface 306 which at least partially leads toward the first locking pin receiving slot 304;

(g) a pivotal first locking pin 308 that is urged about, near or against the ramped surface 306 of the first cam 114 and is capable of selectively entering into and being received or engaged by the first locking pin receiving slot 304 or being removed therefrom;

(h) a pivotal first bracket 310 for holding and urging the first locking pin 308 into operational engagement with the ramped surface 306 of the first cam 14 and/or the first locking pin receiving slot 304;

(i) a first drive motor 100 operatively secured to the pivotal first bracket 310, the weight of the first drive motor 100 and first bracket 310 capable of urging the first locking pin 308 against the ramped surface 306 of the first cam 114 and/or the first locking pin receiving slot 304, the first drive motor 100 also having a first drive shaft 102; and (j) a first frictional contact wheel 112 operatively secured to the first drive shaft 102, wherein the first frictional contact wheel 112 is capable of rotating the first drive wheel 48 and drive the apparatus across the floor 14 when the first frictional contact wheel 112 is urged against and comes into frictional contact with an exterior surface 116 or face of the first drive wheel 48.

Rotation of the first drive wheel 48 and associated first cam 114 about the first generally vertical axis 60 permits the first locking pin 308 to engage and become secured within the first locking pin receiving slot 304 and, thereby, operatively lock the first drive wheel 48 in its first operational position 64. Reverse rotation of the first drive wheel 48 will disengage the first locking pin 308 from the first locking pin receiving slot 304. Continued rotation of the first drive wheel about the first generally vertical axis 60 will move the first drive wheel 48 into its first traveling position 62. Thus positioned and secured, the first drive wheel 48 can be selectively pivoted between the first traveling position 62 and the first operational position 64.

Similarly, as shown within FIGS. 4B and 9B, the second drive wheel engagement mechanism and/or second clutch mechanism 110 of the preferred embodiment comprises a combination of:

(a) the second drive wheel 50;

(b) a second generally horizontal axle 68' passing through or secured to the second drive wheel 50;

(c) a second generally U-shaped wheel support 400 that at least partially surrounds the second drive wheel 50 and to which the second axle 68' is operatively secured;

(d) a second generally vertical axle 72' secured to the second U-shaped wheel support 400;

(e) a second bearing 402 and/or bearing mount secured to or incorporated within the lower chassis 44 which receives and retains the second generally vertical axle 72' and permits rotation of the second U-shaped wheel support 400 and the second drive wheel 50 about the generally vertical axis 72;

(f) a rotatable second cam 120 that generally surrounds the second generally U-shaped wheel support 400, wherein the second cam 120 has a second locking pin receiving slot 404 and a ramped surface 406 which at least partially leads toward the second locking pin receiving slot 404;

(g) a pivotal second locking pin 408 that is urged about, near or against the ramped surface 406 of the second cam 120 and is capable of selectively entering into and being received or engaged by the second locking pin receiving slot 404 or being removed therefrom;

(h) a pivotal second bracket 410 for holding and urging the second locking pin 408 into operational engagement with the ramped surface 406 of the second cam 120 and/or the second locking pin receiving slot 404;

(i) a second drive motor 106 operatively secured to the pivotal second bracket 410, the weight of the second drive motor 106 and second bracket 410 capable of urging the second locking pin 408 against the ramped surface 406 of the second cam 120 and/or the second locking pin receiving slot 404, the second drive motor 106 also having a second drive shaft 108; and (j) a second frictional contact wheel 118 operatively secured to the second drive shaft 108, wherein the second frictional contact wheel 118 is capable of rotating the second drive wheel 50 and drive the apparatus 12 across the floor 14 when the second frictional contact wheel 118 is urged against and comes into frictional contact with an exterior surface 122 or face of the second drive wheel 50.

Rotation of the second drive wheel 50 and associated second cam 120 about the second generally vertical axis 72 permits the second locking pin 408 to engage and become secured within the second locking pin receiving slot 404 and, thereby, operatively lock the second drive wheel 50 in its second operational position 76. Reverse rotation of the second drive wheel 50 will disengage the second locking pin 408 from the second locking pin receiving slot 404. Continued rotation of the second drive wheel about the second generally vertical axis 72 will move the second drive wheel 50 into its second traveling position 74. Thus positioned and secured, the second drive wheel 50 can be selectively pivoted between the second traveling position 74 and the second operational position 76.

Within the preferred embodiment of this invention, the first drive wheel 48 and the second drive wheel 50 are each manually moved between their respective traveling and operational positions. Alternatively, a motor driven mechanism and/or solenoid could be provided to rotate the first drive wheel 48 and/or the second drive wheel 50 between such two positions.

FIGS. 1, 4A, 4B, 12 and 13 illustrate the first drive wheel 48 assuming its first operational position 64. The second drive wheel 50 would assume its second operation position 76 in a similar manner. In these positions, the first clutch mechanism 104 is engaged to the first drive motor 100, and the second clutch mechanism 110 is engaged to the second drive motor 106. The first drive wheel 48 and the second drive wheel 50 are both oriented to move along an X-axis 200 as required during performance of the medical procedure.

FIGS. 8, 9A and 9B illustrate the first drive wheel 48 assuming a first traveling position 62. The second drive wheel 50 would assume a similar a second traveling position 74. In these positions, the first clutch mechanism 104 can be disengaged from the first drive motor 100 and the second clutch mechanism 110 can be disengaged from the second drive motor 106. The first drive wheel 48 and the second drive wheel 50 are both oriented to move along a Y-axis 202 and are positioned for traveling and not positioned for performance of the medical procedure.

Figure 11:
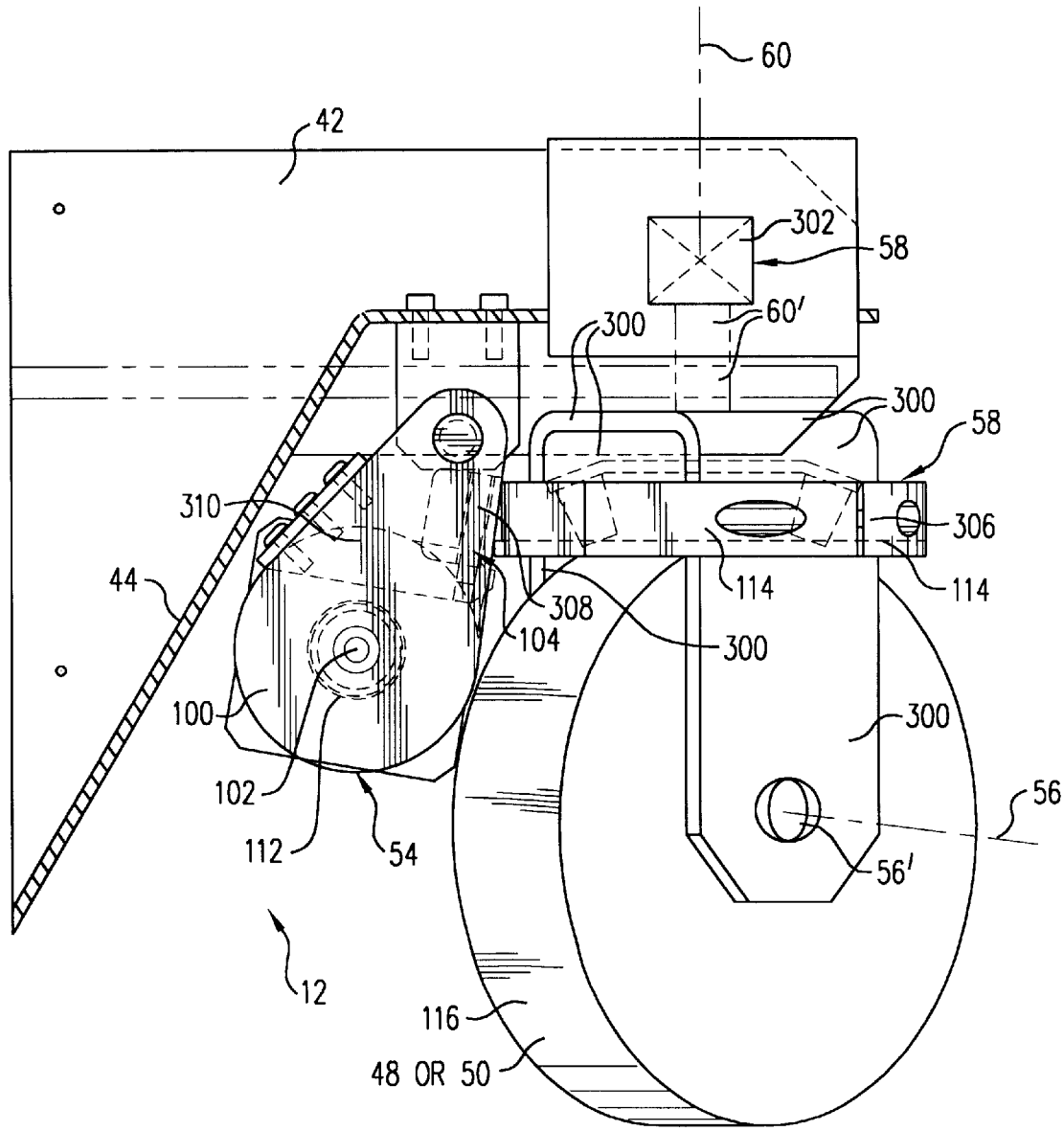
FIG. 11 is a partial, enlarged, cross-sectional, side elevational view of the drive wheel engagement mechanism and the drive wheel rotation mechanism as illustrated within FIG. 10.
Figure 12:
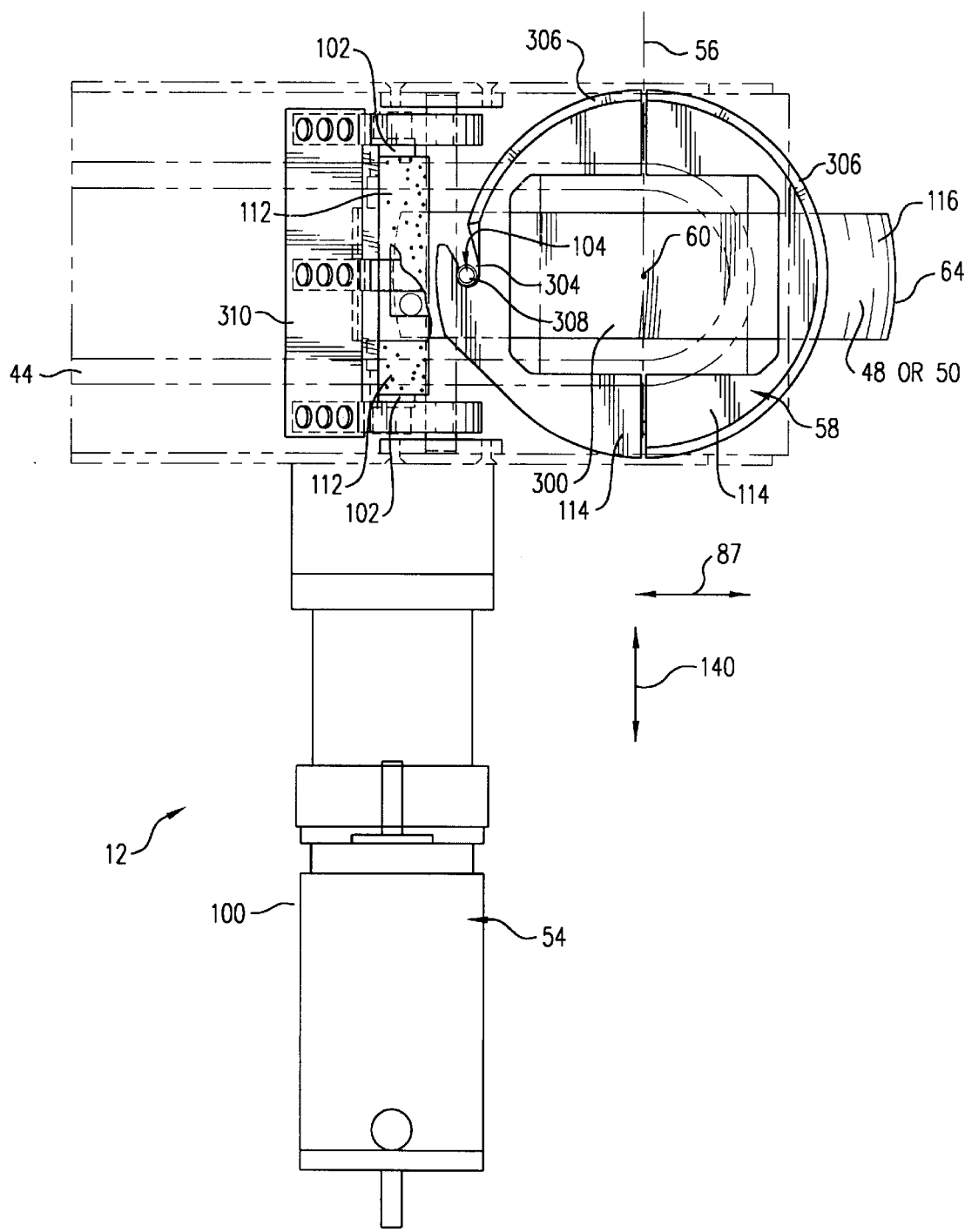
FIG. 12 is a partial, enlarged, schematic, plan view of the drive wheel engagement mechanism in an engaged position.
Figure 13:
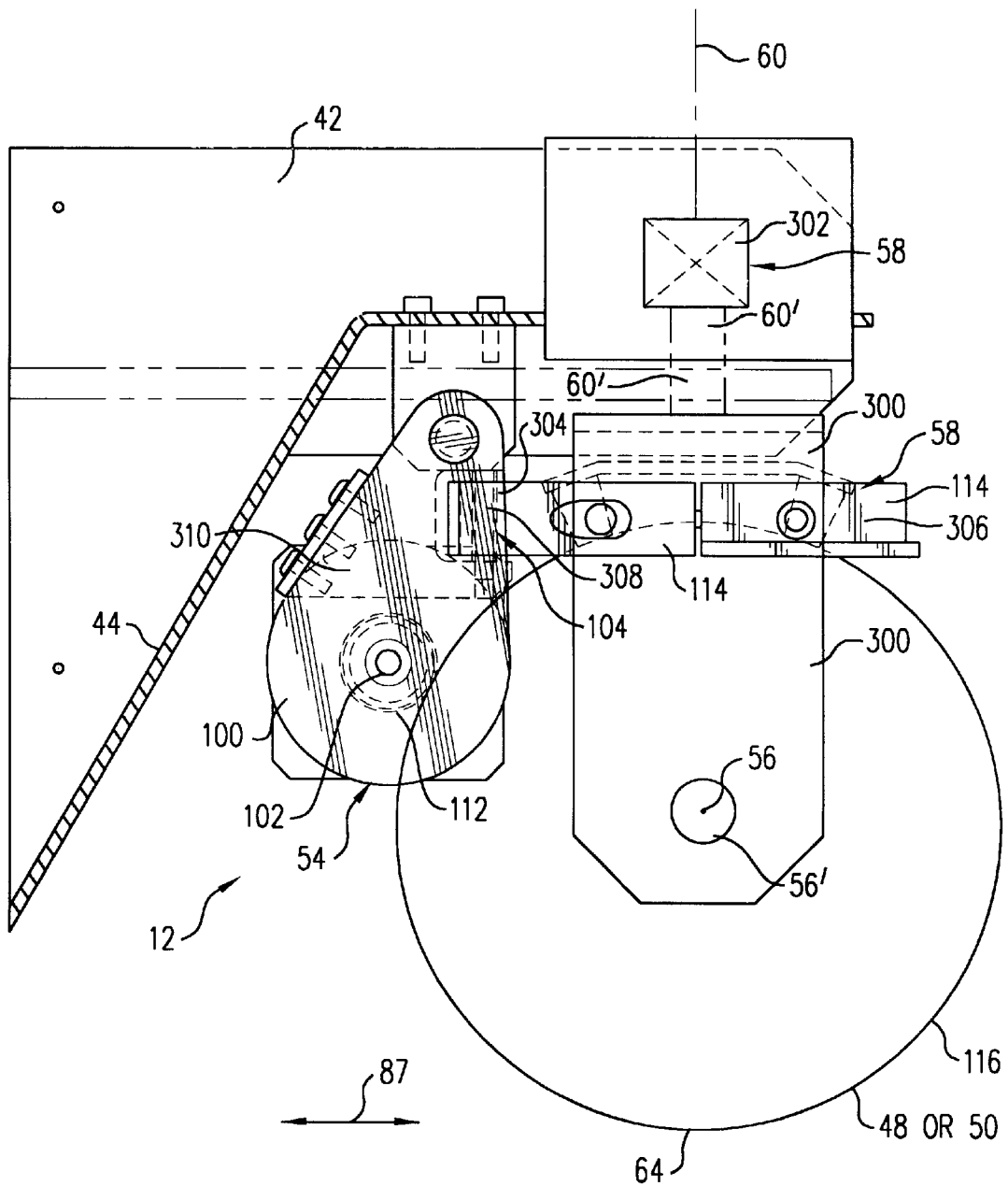
FIG. 13 is a partial, enlarged, cross-sectional, side elevational view of the drive wheel engagement mechanism and the drive wheel rotation mechanism in their locked or engaged position as illustrated within FIG. 12.

FIGS. 10 and 11 illustrate the first drive wheel 48 in a position midway between the first traveling position 62 and the first operational position 64.

Please also recall that the support column 38 permits the scanning and/or imaging means 16 to move upwardly and downwardly along a Z-axis 204.

The apparatus 12 also includes means 58 for selectively rotating the first drive wheel 48 about the first vertical axis 60 between the first traveling position 62 and the first operational position 64. The rotating means 58 may simply comprise a lever or knob that can be rotated to urge the first drive wheel 48 between the first traveling position 62 and the first operational position 64.

Alternatively, the rotating means 58 could include one or more pulleys or drive belts that are operatively secured between the first coupling means 88 and a mechanically or electrically powered first rotator motor, which in turn is operatively secured to the lower chassis 44. Thus positioned, the first rotator motor could be used to rotate the first drive wheel 48.

The means 70 for selectively rotating the second drive wheel 50 about the second generally vertical axis 72 between the second traveling position 74 and the second operational position 76 may similarly comprise a lever or knob that can be rotated to urge the second drive wheel 50 between the second traveling position 74 and the second operational position 76.

Alternatively, the rotating means 70 could include one or more pulleys or drive belts that are operatively secured between the second coupling means 94 and a mechanically or electrically powered second rotator motor, which in turn is operatively secured to the lower chassis 44. Thus positioned, the second rotator motor could be used to rotate the second drive wheel 50.

The first drive wheel 48 is provided with its own first drive motor 100, and the second drive wheel 50 is provided with its own independent second drive motor 106. Rotation of the first drive shaft 102 of the first drive motor 100 transmits rotational power to a first contact wheel 112. When the first drive wheel 48 is rotated to its operational position, a first cam 114 directs the first contact wheel 112 to be urged against and engage an exterior face 116 or portion of the first drive wheel 48. Thus positioned, rotation of the first drive shaft 102 causes the first contact wheel 112 to rotate. When the first contact wheel 112 comes into frictional contact with the first drive wheel 48, such as when the first drive wheel 48 assumes its first operational position 64, the first contact wheel 112 causes the first drive wheel 48 to rotate, thereby, driving the apparatus 12 across the floor 14.

Similarly, rotation of the second drive shaft 108 of the second drive motor 106 transmits rotational power to a second contact wheel 118. When the second drive wheel 50 is rotated to its operational position, a second cam 120 directs the second contact wheel 118 to be urged against and engage an exterior face 122 or portion of the second drive wheel 50. Thus positioned, rotation of the second drive shaft 108 causes the second contact wheel 118 to rotate. When the second contact wheel 118 comes into frictional contact with the second drive wheel 50, such as when the second drive wheel 50 assumes its second operational position 76, the second contact wheel 118 causes the second drive wheel 50 to rotate, thereby, driving the apparatus 12 across the floor 14.

If desired, a reduction gear crankcase could be used to regulate the rotational speed of the first drive shaft 102 and/or the second drive shaft 108.

As explained above, the lower chassis 44 moves along a first path 140, which is generally parallel to the Y-axis 202, when the first drive wheel 48 is in its first traveling position 62 and the second drive wheel 50 is in its second traveling position 74.

However, the lower chassis 44 moves along the second path 87, which is generally parallel to the X-axis 200, when the first drive wheel 48 is in its first operational position 64 and the second drive wheel 50 is in its second operational position 76.

The first traveling position 62 and first path 140 is intended to be generally tangential or perpendicular to the first operational position 64 and second path 87.

Similarly, the second traveling position 74 and is intended to be generally tangential or perpendicular to the second operational position 76.

Furthermore, the first drive wheel 48, the first rotating means 54, the second drive wheel 50, and the second rotating means 66 should be capable of moving the lower chassis 44 in a very precise, predictable, and regulated manner.

If desired, the apparatus 12 may include a protective shield that is secured to the lower chassis 44 to shield the lower chassis 44 from drawing in contaminants and/or debris therein.

The apparatus 12 may also comprise at least one wiper blade or washer secured to the lower chassis 44 about the first drive wheel 48, the second drive wheel 50, and/or the third wheel 52 to further shield the lower chassis 44 from drawing in contaminants and/or debris therein.

Figure 26:
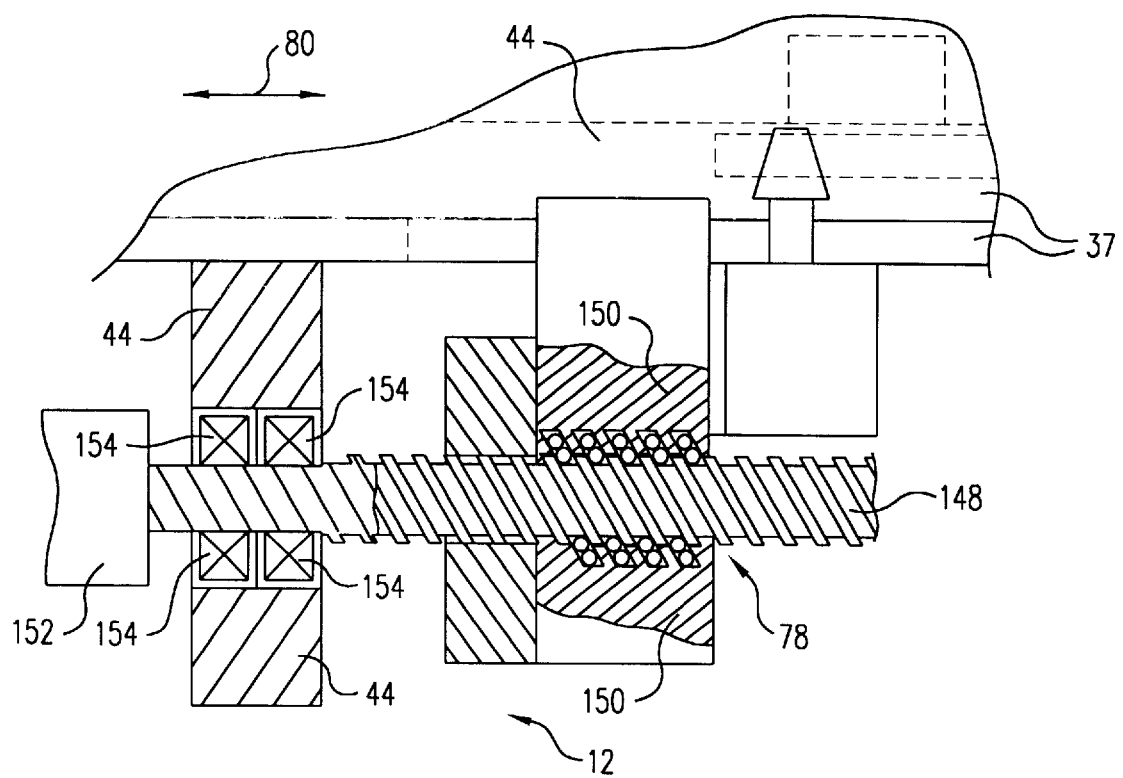
FIG. 26 is an enlarged, partial, cross-sectional, schematic, plan view of the fourth embodiment illustrating in greater detail the drive mechanism for the extension arm.

As best seen within FIGS. 24 through 26, the means 78 for mechanically or electrically moving the upper chassis 37 in a selective and controlled manner along the predetermined path 80 relative to the lower chassis 44 between the retracted position 82 and the extended position 84 may include use of: (a) a worm-screw 148 that is operatively secured to the lower chassis 44 or, in the alternative, to the upper chassis 37; (b) a drive nut 150 that is operatively secured to the upper chassis 37 or, in the alternative, to the lower chassis 44, and operatively engages the worm-screw 148; and (c) a scanner motor 152 that is operatively connected to the worm-screw 148 and to the lower chassis 44 or, in the alternative, to the upper chassis 37, to selectively rotate the worm-screw 148 in a predetermined and controlled manner.

The rotary motion of the worm screw 148 translates into linear motion via the drive nut 150 or a ball screw and recirculating ball nut assembly. For example, the ball screw or worm screw 148 could be mounted generally to a top or upper portion of the lower chassis 44, between and generally parallel to the linear ball rails or tracks 86. The worm screw 148 is thus mounted via use of pillow block bearings 154 which are attached to each end of the worm screw 148 in such a way as to capture the worm screw 148 axially, yet allow rotary motion of the worm screw 148. The ball screw or worm screw 148 threads through the ball nut 150 in such a way as to cause the ball nut 150 to move forward and back along the length of the worm screw 148 as the worm screw 148 is rotated. With the recirculating ball nut 150 being fixed to the movable upper chassis 37, the rotation of the worm screw 148 causes the upper chassis 37 to move forward and backward depending upon the direction of rotation of the worm screw 148.

Alternatively, the means 78 for mechanically or electrically moving the upper chassis 37 in a selective and controlled manner along the predetermined path relative to the lower chassis 44 between the retracted position 82 and the extended position 84 may include use of: (a) a worm-screw 148 that is operatively secured to the upper chassis 37; (b) the drive nut 150 could be operatively secured to the lower chassis 44 and operatively engage the worm-screw 148; and (c) the scanner motor 152 is operatively connected to the worm-screw 148 and to the upper chassis 37 to selectively rotate the worm-screw 148 in a predetermined and controlled manner.

The position of the scanner motor 152 relative to the lower chassis 44 or upper chassis 37 is not determinative. For example, the scanner motor 152 may be secured to the lower chassis 44 or upper position at a rearward position, forward position or at any position therebetween.

As illustrated within FIGS. 20 and 21, the means 78 for mechanically or electrically moving the upper chassis 37 in a selective and controlled manner along the predetermined path 80 relative to the lower chassis 44 between the retracted position 82 and the extended position 84 may include use of a rack 156 and pinion 158 system. For example, the rack 156 or timing belt may be operatively secured to the upper chassis 37. The pinion 156, toothed gear, or combination of pinion 156, toothed gear and follower pulleys or wheels 160, can be operatively secured to a powered rack and pinion drive motor 162, which in turn is operatively secured to the lower chassis 44. Teeth on the pinion 156 engage corresponding teeth on the rack 154 or timing belt to move the upper chassis 37 back and forth along the Y-axis 202 in a predetermined and controlled manner.

Within the preferred embodiment of this invention, the cabinet 42 or cowling is either operatively secured to the apparatus 12 or is incorporated therein. More particularly, the cabinet 42 is either operatively secured to the lower chassis 44 or is incorporated therein.

The cabinet 42 may be provided with a handle 164 which is secured thereto. The handle 164 can be used to help assist in steering, pushing and/or pulling the apparatus 12 along a corridor or hallway.

Of course the various motors included within this invention can be selectively powered. As shown within FIG. 1, an electrical chord 166 can be plugged into a conventional electrical power outlet to provide electrical power to such motors.

Alternatively, one or more batteries 168 could be operatively connected to such motors to provide electrical power thereto. For example, the batteries 168 could be transported and stored within the cabinet 42 as shown within FIG. 1.

To operate and control the various motors within the apparatus 12, the cabinet 42 may be provided with a permanently installed control panel. Alternatively, or in addition thereto, a hand-held control panel 170 may be provided. Control panel and/or hand-held control panel 170 may be used to activate and/or deactivate the scanning and/or imaging means 16, the transmitter 26, the curved guide means 34, the raising and lowering of the support column 38, the rotating means 54, the rotating means 58, the rotating means 66, the rotating means 70, and the moving means 78. More particularly, the control panel 170 may be used to activate and/or deactivate such elements as: the first drive motor 100, the first clutch mechanism 104, the second drive motor 106, the second clutch mechanism 110, the scanner motor 152, and/or the rack and pinion drive motor 162.

In addition, the receiver 30 or image intensifier can be secured to the C-arm 24 in such a manner as to enable its position to be adjusted. For example, the source to image distance between the transmitter 26 or x-ray tube and the receiver 30 can be variable and adjustable.

Figure 2:
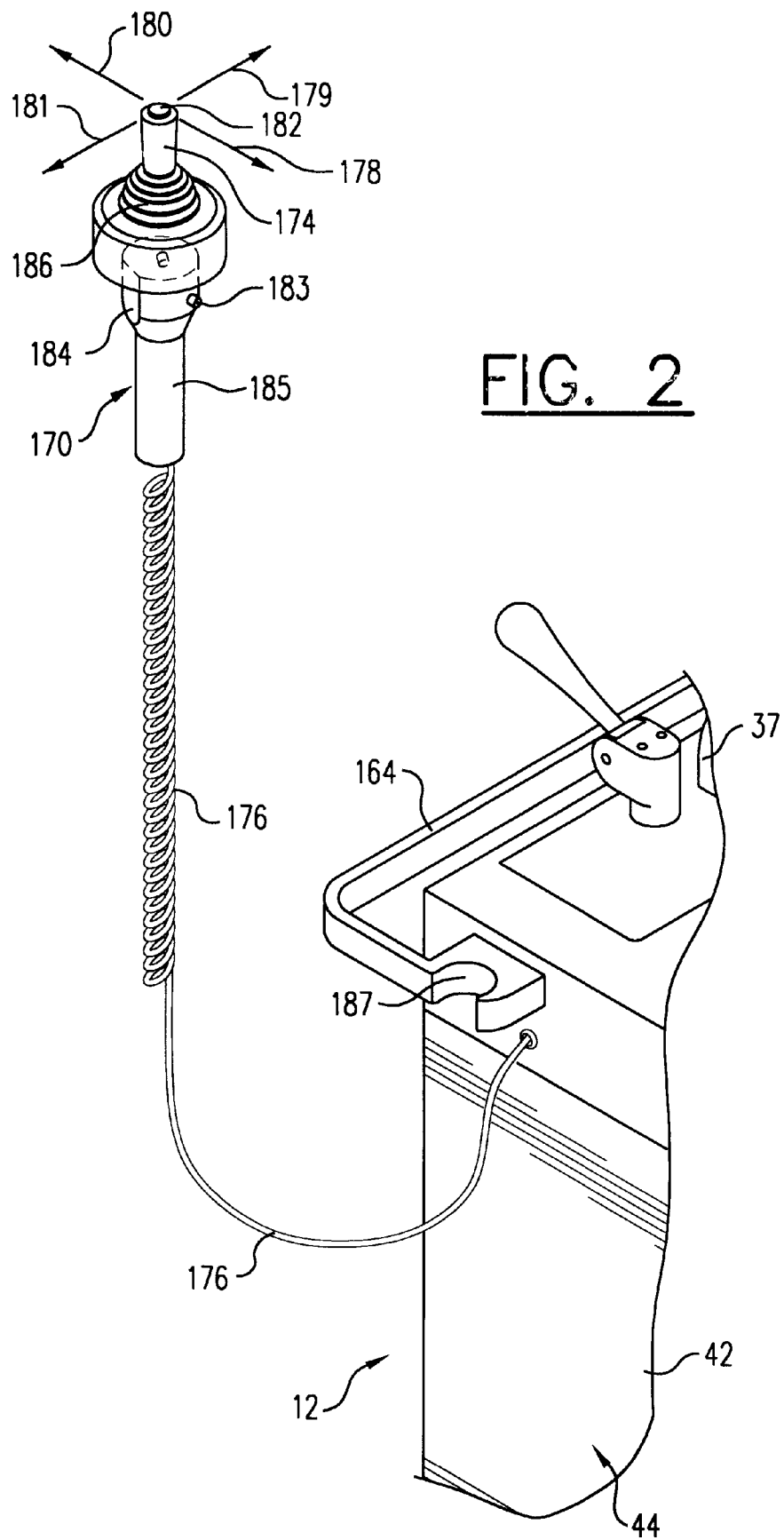
FIG. 2 is a partial, schematic and perspective view of a preferred control mechanism operatively attached to a cabinet and associated internal machinery of this invention to control the activation and movement of one or more drive wheels, an upper chassis or extension arm, a C-arm and/or imaging equipment.
Figure 3:
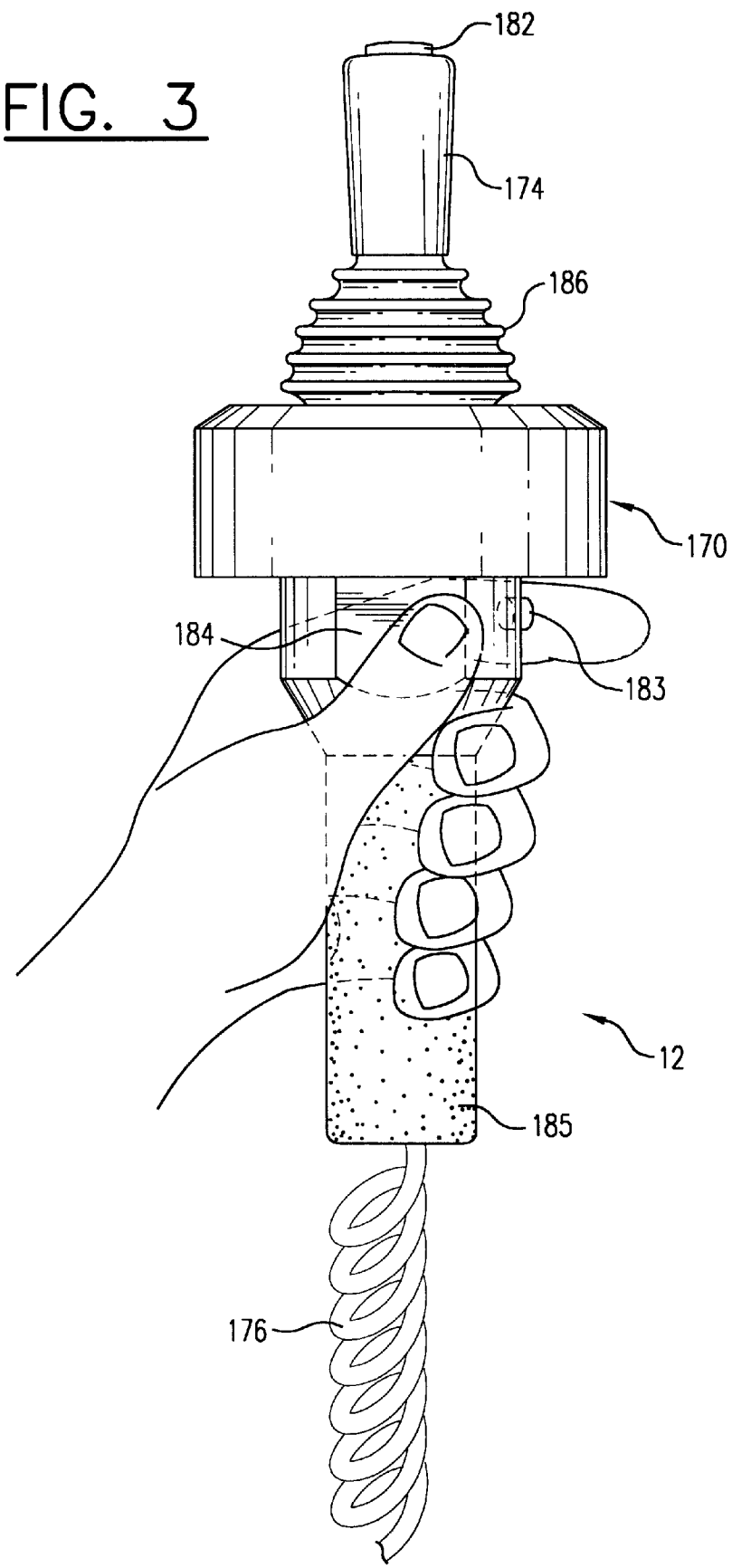
FIG. 3 is a partial, enlarged, side elevational view of the preferred control mechanism illustrated within FIG. 2 being held by an operator.
Figure 4A:
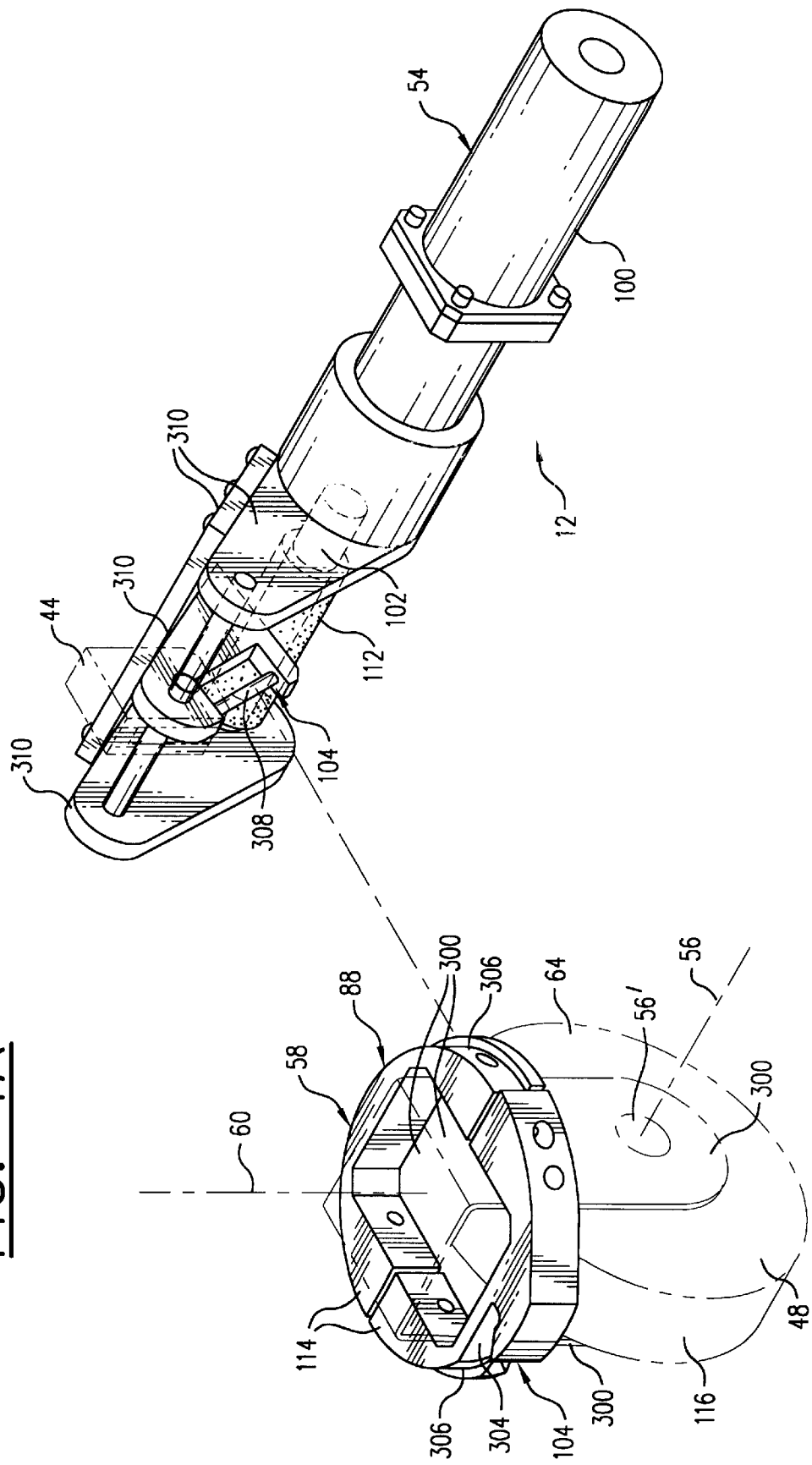
FIG. 4A is a partial, enlarged, exploded, schematic and perspective view of a first drive wheel, a first drive wheel engagement mechanism and a first drive wheel rotation mechanism.
Figure 6:
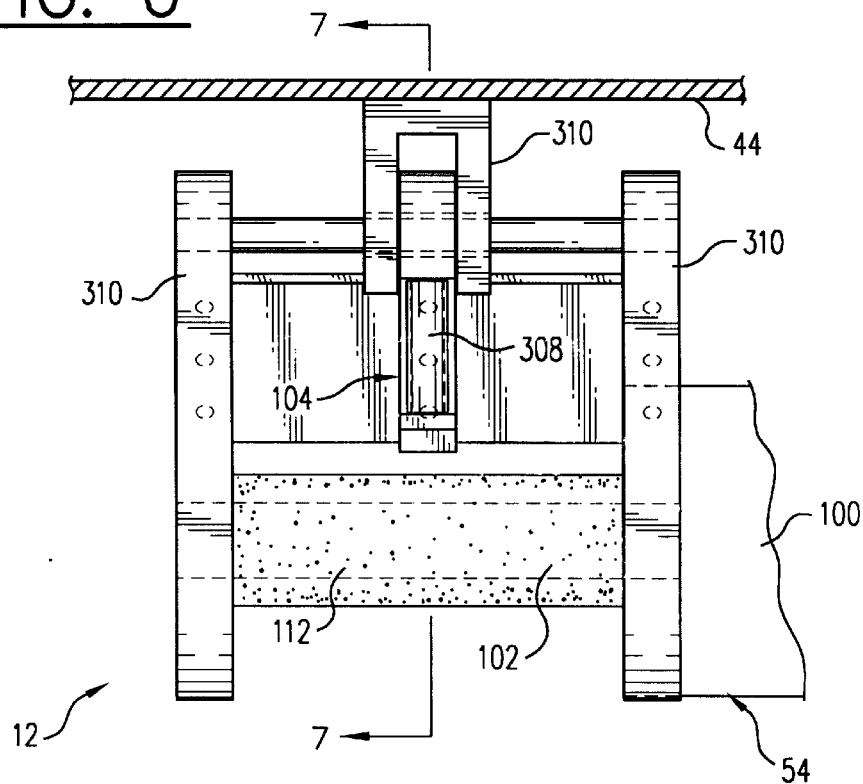
FIG. 6 is a partial, enlarged, cross-sectional and front elevational view of a locking pin and associated housing or boss as contained within the drive wheel engagement mechanism illustrated within FIG. 4. The locking pin illustrated within FIG. 6 can be used to selectively and removably engage and lock the drive wheel engagement cam mechanism illustrated within FIG. 5.
Figure 7:
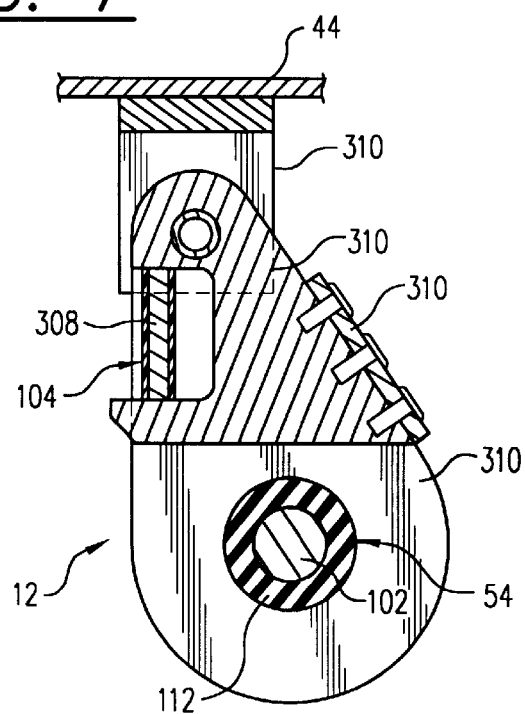
FIG. 7 is a partial, enlarged, cross-sectional and side elevational view of the locking pin, associated housing or boss, and contact wheel illustrated within FIG. 6.

The control panel and/or hand-held control panel 170 may include a traditional computer keyboard, a specially designed keyboard having directional keys thereon, a computer pointing device, a rotating ball similar to that of a computer mouse, and/or a computer joystick 174. The joystick 174 can be used to convert simple hand movements into complex combinations of directional instructions for the apparatus 12, as generally shown by arrows 178, 179, 180 and 181 in FIG. 2, and any direction or combination of directions therebetween. Furthermore, joystick 174 may include one or more switches of buttons 182 and 183 thereon to control particular movements of the apparatus 12.

To expedite and assist the operator to obtain a proper orientation of the control panel 170, a generally flat portion 184 or location indicator may be used.

The control panel 170 also has a handle 185 which can be held by the operator, and a generally flexible jacket 186 about the joystick 174 to prevent debris or dust from fowling the electronics contained within the control panel 170.

The handle 164 may be provided with a recess or receptacle 187 into which the control panel 170 may be placed and retained.

The control panel 170 is preferably a handle-held control unit that is either remotely controlled, via an elongated attached electrical chord 176, is radio controlled, and/or is infrared controlled. By using a remote, radio, and/or infrared controlled control panel 170, an operator can stand adjacent to the patient or at a distance, depending upon the needs of the particular medical procedure.

The means and construction disclosed herein are by way of example and comprise primarily the preferred and several alternative forms of putting the invention into effect. Although the drawings depict the preferred and several alternative embodiments of the invention, other embodiments are described within the preceding and following text. One skilled in the art will appreciate that the disclosed apparatus and devices may have a wide variety of designs, shapes and configurations. Additionally, persons skilled in the art to which the invention pertains might consider the foregoing teachings in making various modifications, other embodiments and alternative forms of the invention.

It is, therefore, to be understood that this invention is not limited to the particular embodiments or specific features shown herein. To the contrary, the invention is claimed in all of its various forms, including all alternatives, modifications, equivalents and alternative embodiments that fall within the legitimate and valid scope of the Claims, appropriately interpreted under the Doctrine Of Equivalents.

INDUSTRIAL APPLICABILITY

This invention may be used by any surgeon, doctor, nurse, technician or other person who is licensed and/or authorized to operate medical scanning equipment. For example, the apparatus and methods of this invention may be used within hospitals, clinics, nursing homes, doctor's offices, military field hospitals, and the like. In essence, the present invention may be used by any person who could benefit from the simple, reliable, easily used apparatus and methods that this invention provides. The apparatus of this invention is compact, unobtrusive, efficient, reusable, durable, rugged, is easily constructed, and is inexpensive and economical to manufacture.

Traditional or nontraditional manufacturing equipment and procedures may be used to manufacture the apparatus of this invention without requiring significant alteration thereto to accomplish the purposes taught herein.

Once manufactured, the apparatus of this invention can be easily transported, used and stored using a minimum amount of operational and storage space for using such imaging equipment. Consequently, the invention also minimizes the size and cargo space required to contain and ship the apparatus. This in turn, reduces transportation and storage costs.

The current invention has a special benefit of being able to incorporate therein mass produced and commercially available medical scanning equipment and machinery that are readily purchasable at medical supply dealers throughout the world. Furthermore, since mass produced medical scanners can be used, the manufacturer of this invention can purchase such scanning equipment and replacement parts related thereto at very competitive prices.

The apparatus of this invention can be used with a wide variety of different medical scanning equipment. Consequently, it is anticipated that the potential consumer base for this invention will be significantly broader than what would have been available for the heretofore known devices. The scope and versatility of the present invention is also much broader than the previously known devices.

Although the invention has a wide range of applications, the invention has special application within interventional and/or endovascular procedures. The present invention permits such procedures to be accomplished in multiple rooms. This invention requires that only a minimum amount of effort be exerted to initially position the apparatus adjacent to the patient. Thereafter, the operator will have nearly unlimited ability to precisely move the medical scanning equipment toward or away from the patient, back and forth along the length of the patient, and above, below and around the patient in a nearly unlimited range of orientations with respect to the patient. This invention increases the speed and accuracy and simplifies the methods required to perform such medical procedures. This in turn provides a greater degree of accuracy and reliability in the gathered data upon which the medical professional will stake his or her professional reputation, with less complications for the user, and is safer for the patient.

Ease and convenience in use is dramatically increased over the prior known devices. The complexity of the apparatus as compared to the prior known devices is greatly reduced. The bulkiness of the apparatus can be minimized to create a streamlined easily cleaned and sanitized apparatus.

We claim:

1. An apparatus supportable upon a floor for moving medical scanning equipment about a portion of a body of a patient, said apparatus comprising a combination of:
    (a) a lower chassis or housing positioned above the floor;
    (b) a first wheel operatively secured to said lower chassis, said first wheel capable of being rotated about a first generally horizontal axis and a first generally vertical axis;
    (c) a second wheel operatively secured to said lower chassis, said second wheel capable of being rotated about a second generally horizontal axis and a second generally vertical axis, said first wheel and said second wheel arranged to support said lower chassis upon the floor and enable movement of said lower chassis relative to the floor;
    (d) remotely actuated means for selectively rotating said first wheel about said first vertical axis between a first traveling position and a first operational position, said first traveling position being generally tangential or perpendicular to said first operational position;
    (e) remotely actuated means for selectively rotating said second wheel about said second vertical axis between a second traveling position and a second operational position, said second traveling position being generally tangential or perpendicular to said second operational position;
    (f) remotely actuated means for mechanically or electrically rotating said first wheel about said first horizontal axis in a selectively controlled manner;
    (g) remotely actuated means for mechanically or electrically rotating said second wheel about said second horizontal axis in a selectively controlled manner, said lower chassis moving along a first path when said first wheel is in said first traveling position and said second wheel is in said second traveling position, said lower chassis moving along a second path when said first wheel is in said first operational position and said second wheel is in said second operational position;
    (h) a rotatable, omnidirectional, third wheel operatively secured to said lower chassis to provide support and stability to said lower chassis, said third wheel permitting movement of said lower chassis directions generally parallel to or horizontal with the floor;
    (i) an upper chassis or extension arm operatively and movably secured to said lower chassis; and
    (j) means for mechanically or electrically moving said upper chassis in a selective and controlled manner along a predetermined third path relative to said lower chassis between a retracted position and an extended position.

2. The apparatus of claim 1, further comprising a protective shield secured to said lower chassis to shield said lower chassis from drawing in contaminants or debris.

3. The apparatus of claim 2, further comprising at least one wiper blade or washer secured to said lower chassis about said first wheel and about said second wheel to shield said lower chassis from drawing in contaminants or debris.

4. The apparatus of claim 1, wherein said first wheel and said second wheel are drive wheels capable of moving said lower chassis in a precise and predictable manner.

5. The apparatus of claim 1, further comprising:
    (a) means for coupling said first wheel to said lower chassis, said first coupling means enabling said first wheel to rotate about said first generally horizontal axis and to rotate about said first vertical axis; and
    (b) means for coupling said second wheel to said lower chassis, said second coupling means enabling said second wheel to rotate about said second generally horizontal axis and to rotate about said second vertical axis.

6. The apparatus of claim 5, wherein said means for selectively rotating said first wheel about said first vertical axis between said first traveling position and said first operational position further comprises a first mechanically or electrically operated lever operatively secured to said means for coupling said first wheel to said lower chassis.

7. The apparatus of claim 6, wherein said means for selectively rotating said second wheel about said second vertical axis between said second traveling position and said second operational position further comprises a second mechanically or electrically operated lever operatively secured to said means for coupling said second wheel to said lower chassis.

8. The apparatus of claim 1, wherein said means for mechanically or electrically rotating said first wheel about said first horizontal axis in a selectively controlled manner comprises a first drive motor operatively secured to said lower chassis.

9. The apparatus of claim 8, wherein said means for mechanically or electrically rotating said second wheel about said second horizontal axis in a selectively controlled manner comprises a second drive motor operatively secured to said lower chassis.

10. The apparatus of claim 1, wherein said lower chassis or housing further comprises one or more tracks into which at least a portion of said upper chassis or extension arm is operatively and movably secured.

11. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a rack operatively secured to said upper chassis;
   (b) a drive rod or drive pinion operatively secured to said lower chassis and operatively engaged with said rack; and
   (c) an extension arm drive motor operatively connected to said drive rod or drive pinion to selectively rotate said drive rod or drive pinion to urge said rack to move said upper chassis in a predetermined and controlled manner relative to said lower chassis.

12. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a rack operatively secured to said lower chassis;
   (b) a drive rod or drive pinion operatively secured to said upper chassis and operatively engaged with said rack; and
   (c) an extension arm drive motor operatively connected to said drive rod or drive pinion to selectively rotate said drive rod or drive pinion to urge said rack to move said upper chassis in a predetermined and controlled manner relative to said lower chassis.

13. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a flexible drive belt operatively secured to said upper chassis;
   (b) a drive rod or drive pinion operatively secured to said lower chassis and operatively engaged with said flexible drive belt; and
   (c) an extension arm drive motor operatively connected to said drive rod or drive pinion to selectively rotate said drive rod or drive pinion to urge said flexible drive belt to move said upper chassis in a predetermined and controlled manner relative to said lower chassis.

14. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a flexible drive belt operatively secured to said lower chassis;
   (b) a drive rod or drive pinion operatively secured to said upper chassis and operatively engaged with said flexible drive belt; and
   (c) an extension arm drive motor operatively connected to said drive rod or drive pinion to selectively rotate said drive rod or drive pinion to urge said flexible drive belt to move said upper chassis in a predetermined and controlled manner relative to said lower chassis.

15. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a worm-screw operatively secured to said upper chassis;
   (b) a drive nut operatively secured to said lower chassis and operatively engaged with said worm-screw; and
   (c) an extension arm drive motor operatively connected to said worm-screw to selectively rotate said worm-screw in a predetermined and controlled manner.

16. The apparatus of claim 1, wherein said means for mechanically or electrically moving said upper chassis or extension arm in a selective and controlled manner along said predetermined third path relative to said lower chassis or housing between said retracted position and said extended position comprises:
   (a) a worm-screw operatively secured to said lower chassis;
   (b) a drive nut operatively secured to said upper chassis and operatively engaged with said worm-screw; and
   (c) an extension arm drive motor operatively connected to said worm-screw to selectively rotate said worm-screw in a predetermined and controlled manner.

17. The apparatus of claim 1, further comprising a cabinet operatively secured to said lower chassis.

18. The apparatus of claim 17, further comprising a handle secured to said cabinet.

19. The apparatus of claim 17, wherein said upper chassis supports and further comprises means for conducting a medical scan of a portion of the body of the patient.

20. The apparatus of claim 19, wherein said means for conducting a medical scan of a portion of the body of the patient comprises a mobile: x-ray-imaging system, a C-arm x-ray-imaging system, an angiographic-imaging system, a cardiac-imaging system, a thermal-imaging system, an ultrasonic-imaging system, or a magnetic-resonance-imaging system.

21. The apparatus of claim 1, further comprising a hand-held control unit to activate or deactivate:
   (a) said means for rotating said first wheel about said first horizontal axis to move said lower chassis along said second path;
   (b) said means for rotating said second wheel about said second horizontal axis to move said lower chassis along said second path; or
   (c) said means for moving said upper chassis in a selective and controlled manner along a predetermined third path relative to said lower chassis between a retracted position and an extended position.

22. The apparatus of claim 21, wherein said hand-held control unit is remote controlled, radio controlled, or infra-red controlled.

* * * * *